United States Patent
Anderson et al.

(10) Patent No.: US 7,179,638 B2
(45) Date of Patent: Feb. 20, 2007

(54) MICROARRAYS AND THEIR MANUFACTURE BY SLICING

(75) Inventors: N. Leigh Anderson, Washington, DC (US); Norman G. Anderson, Rockville, MD (US); James A. Braatz, Beltsville, MD (US)

(73) Assignee: Large Scale Biology Corporation, Vacaville, CA (US)

( * ) Notice: Subject to any disclaimer, the term of this patent is extended or adjusted under 35 U.S.C. 154(b) by 686 days.

(21) Appl. No.: 10/061,969

(22) Filed: Jan. 25, 2002

(65) Prior Publication Data
US 2003/0044855 A1    Mar. 6, 2003

Related U.S. Application Data

(63) Continuation-in-part of application No. 09/628,339, filed on Jul. 28, 2000, now Pat. No. 6,846,635, which is a continuation-in-part of application No. 09/482,460, filed on Jan. 13, 2000, now Pat. No. 6,713,309.

(60) Provisional application No. 60/146,653, filed on Jul. 30, 1999.

(51) Int. Cl.
*C12M 1/34* (2006.01)

(52) U.S. Cl. .............. 435/287.2; 422/57; 422/58; 435/6; 435/287.1; 436/518; 436/524; 436/525; 436/527

(58) Field of Classification Search ........... 422/57, 422/58; 435/6, 287.1, 287.2; 436/518, 524, 436/525, 527
See application file for complete search history.

(56) References Cited

U.S. PATENT DOCUMENTS

| | | | |
|---|---|---|---|
| 4,238,757 A | 12/1980 | Schenck |
| 4,459,360 A | 7/1984 | Marinkovich |
| 4,623,355 A | 11/1986 | Sawruk |
| 4,708,931 A | 11/1987 | Christian |
| 4,896,363 A | 1/1990 | Taylor et al. |
| 4,981,653 A | 1/1991 | Marino |
| 5,186,824 A | 2/1993 | Anderson |
| 5,252,743 A | 10/1993 | Barrett et al. |
| 5,264,565 A | 11/1993 | Barrett et al. |
| 5,273,656 A | 12/1993 | Anderson et al. |
| 5,302,707 A | 4/1994 | Campbell et al. |
| 5,324,633 A | 6/1994 | Fodor et al. |
| 5,338,665 A | 8/1994 | Schatz et al. |

(Continued)

FOREIGN PATENT DOCUMENTS

DE    19823454    11/1999

(Continued)

OTHER PUBLICATIONS

Arnold MA., "Enzyme-based fiber optic sensor." *Anal Chem* (1985) 57:565-566.

(Continued)

*Primary Examiner*—Christopher L. Chin
(74) *Attorney, Agent, or Firm*—John E. Tarcza; Thomas Gallegos; Wayne P. Fitzmaurice

(57) ABSTRACT

Microarrays are prepared by using a separate fiber for each compound being used in the microarray. The fibers are bundled and sectioned to form a thin microarray that may be glued to a backing.

19 Claims, 8 Drawing Sheets

U.S. PATENT DOCUMENTS

| | | | |
|---|---|---|---|
| 5,362,899 A | 11/1994 | Campbell | |
| 5,420,328 A | 5/1995 | Campbell | |
| 5,424,186 A | 6/1995 | Fodor et al. | |
| 5,432,018 A | 7/1995 | Barrett et al. | |
| 5,451,683 A | 9/1995 | Barrett et al. | |
| 5,482,867 A | 1/1996 | Barrett et al. | |
| 5,491,074 A | 2/1996 | Aldwin et al. | |
| 5,498,530 A | 3/1996 | Schatz et al. | |
| 5,527,681 A | 6/1996 | Holmes | |
| 5,540,828 A | 7/1996 | Yacynych | |
| 5,545,531 A | 8/1996 | Rava et al. | |
| 5,571,639 A | 11/1996 | Hubbell et al. | |
| 5,578,832 A | 11/1996 | Trulson et al. | |
| 5,585,275 A | 12/1996 | Hudson et al. | |
| 5,585,646 A | 12/1996 | Kossovsky et al. | |
| 5,593,839 A | 1/1997 | Hubbell et al. | |
| 5,607,691 A | 3/1997 | Hale et al. | |
| 5,622,944 A | 4/1997 | Hale et al. | |
| 5,624,711 A | 4/1997 | Fujimoto et al. | |
| 5,635,597 A | 6/1997 | Barrett et al. | |
| 5,648,458 A | 7/1997 | Cwirla et al. | |
| 5,654,276 A | 8/1997 | Barrett et al. | |
| 5,655,560 A | 8/1997 | Kedar et al. | |
| 5,668,110 A | 9/1997 | Barrett et al. | |
| 5,670,322 A * | 9/1997 | Eggers et al. | 435/6 |
| 5,677,195 A | 10/1997 | Winkler et al. | |
| 5,690,894 A | 11/1997 | Pinkel et al. | |
| 5,710,000 A | 1/1998 | Sapolsky et al. | |
| 5,723,584 A | 3/1998 | Schatz | |
| 5,728,802 A | 3/1998 | Barrett et al. | |
| 5,733,729 A | 3/1998 | Lipshutz et al. | |
| 5,739,386 A | 4/1998 | Holmes | |
| 5,744,305 A | 4/1998 | Fodor et al. | |
| 5,751,629 A | 5/1998 | Nova et al. | |
| 5,759,779 A | 6/1998 | Dehlinger | |
| 5,763,175 A | 6/1998 | Brenner | |
| 5,767,234 A | 6/1998 | Yanofsky et al. | |
| 5,770,456 A | 6/1998 | Holmes | |
| 5,786,331 A | 7/1998 | Barrett et al. | |
| 5,811,238 A | 9/1998 | Stemmer et al. | |
| 5,817,751 A | 10/1998 | Szardenings et al. | |
| 5,834,758 A | 11/1998 | Trulson et al. | |
| 5,843,655 A | 12/1998 | McGall | |
| 5,843,767 A | 12/1998 | Beattie | |
| 5,851,772 A | 12/1998 | Mirzabekov et al. | |
| 5,856,101 A | 1/1999 | Hubbell et al. | |
| 5,861,247 A | 1/1999 | Mirzabekov et al. | |
| 5,874,214 A | 2/1999 | Nova et al. | |
| 5,874,219 A | 2/1999 | Rava et al. | |
| 5,880,096 A | 3/1999 | Barrett et al. | |
| 5,885,837 A | 3/1999 | Winkler et al. | |
| 5,917,016 A | 6/1999 | Holmes | |
| 5,922,545 A | 7/1999 | Dower et al. | |
| 5,925,562 A | 7/1999 | Nova et al. | |
| 5,932,433 A | 8/1999 | Schatz | |
| 5,932,579 A | 8/1999 | Campbell et al. | |
| 5,945,334 A | 8/1999 | Besemer et al. | |
| 5,945,522 A | 8/1999 | Cohen et al. | |
| 5,961,923 A | 10/1999 | Nova et al. | |
| 5,968,740 A | 10/1999 | Fodor et al. | |
| 5,974,164 A | 10/1999 | Chee | |
| 5,981,734 A | 11/1999 | Mirzabekov et al. | |
| 5,990,112 A | 11/1999 | Campbell et al. | |
| 5,993,627 A | 11/1999 | Anderson et al. | |
| 6,013,440 A | 1/2000 | Lipshutz et al. | |
| 6,022,963 A | 2/2000 | McGall et al. | |
| 6,025,129 A | 2/2000 | Nova et al. | |
| 6,025,601 A | 2/2000 | Trulson et al. | |
| 6,027,880 A | 2/2000 | Cronin et al. | |
| 6,027,894 A | 2/2000 | Sapolsky et al. | |
| 6,060,288 A | 5/2000 | Adams et al. | |
| 6,140,135 A | 10/2000 | Landegren et al. | |
| 6,210,910 B1 | 4/2001 | Walt et al. | |
| 6,329,209 B1 | 12/2001 | Wagner et al. | |
| 6,350,618 B1 * | 2/2002 | Borrelli et al. | 436/174 |
| 6,365,418 B1 | 4/2002 | Wagner et al. | |
| 6,406,921 B1 | 6/2002 | Wagner et al. | |
| 6,454,924 B2 | 9/2002 | Jedrzejewski et al. | |
| 6,475,808 B1 | 11/2002 | Wagner et al. | |
| 6,475,809 B1 | 11/2002 | Wagner et al. | |
| 6,576,478 B1 | 6/2003 | Wagner et al. | |
| 6,582,969 B1 | 6/2003 | Wagner et al. | |
| 6,596,545 B1 | 7/2003 | Wagner et al. | |
| 6,630,358 B1 | 10/2003 | Wagner et al. | |
| 6,656,725 B2 | 12/2003 | Mirzabekov et al. | |
| 6,682,893 B2 | 1/2004 | Taylor et al. | |
| 6,682,942 B1 | 1/2004 | Wagner et al. | |
| 6,686,154 B2 | 2/2004 | Mock et al. | |
| 6,720,157 B2 | 4/2004 | Indermuhle et al. | |
| 6,730,516 B2 | 5/2004 | Jedrzejewski et al. | |
| 6,780,582 B1 | 8/2004 | Wagner et al. | |
| 6,794,197 B1 | 9/2004 | Indermuhle et al. | |
| 6,897,073 B2 | 5/2005 | Wagner et al. | |

FOREIGN PATENT DOCUMENTS

| | | |
|---|---|---|
| EP | 274824 | 7/1988 |
| EP | 708483 | 4/1996 |
| EP | 717113 | 6/1996 |
| EP | 721016 | 7/1996 |
| EP | 728520 | 8/1996 |
| EP | 785280 | 7/1997 |
| EP | 799897 | 10/1997 |
| EP | 812922 | 12/1997 |
| EP | 913507 | 1/1998 |
| EP | 848067 | 6/1998 |
| EP | 926260 | 6/1999 |
| EP | 953210 | 8/1999 |
| EP | 950720 | 10/1999 |
| EP | 955085 | 11/1999 |
| EP | 955382 | 11/1999 |
| EP | 961174 | 12/1999 |
| EP | 967217 | 12/1999 |
| GB | 2262163 | 6/1993 |
| JP | 63010560 | 1/1988 |
| JP | 63010561 | 1/1988 |
| JP | 63010562 | 1/1988 |
| JP | 63010563 | 1/1988 |
| JP | 63010564 | 1/1988 |
| JP | 63010565 | 1/1988 |
| JP | 63172454 | 7/1988 |
| JP | 1213662 | 8/1989 |
| JP | 5109722 | 4/1993 |
| JP | 6085240 | 3/1994 |
| JP | 6256753 | 9/1994 |
| WO | 8302669 | 8/1983 |
| WO | 8703965 | 7/1987 |
| WO | 8808875 | 11/1988 |
| WO | 9015070 | 12/1990 |
| WO | 9107087 | 5/1991 |
| WO | 9117271 | 11/1991 |
| WO | 9119818 | 12/1991 |
| WO | 9210092 | 6/1992 |
| WO | 9210587 | 6/1992 |
| WO | 9210588 | 6/1992 |
| WO | 9306121 | 4/1993 |
| WO | 9308278 | 4/1993 |
| WO | 9309668 | 5/1993 |
| WO | 9310161 | 5/1993 |
| WO | 9311565 | 6/1993 |
| WO | 9322680 | 11/1993 |
| WO | 9322684 | 11/1993 |
| WO | 9325197 | 12/1993 |
| WO | 9406808 | 3/1994 |

| | | |
|---|---|---|
| WO | 9410128 | 5/1994 |
| WO | 9417792 | 8/1994 |
| WO | 9418345 | 8/1994 |
| WO | 9425043 | 11/1994 |
| WO | 9428173 | 12/1994 |
| WO | 9500530 | 1/1995 |
| WO | 9504069 | 2/1995 |
| WO | 9511922 | 5/1995 |
| WO | 9511988 | 5/1995 |
| WO | 9511995 | 5/1995 |
| WO | 9512608 | 5/1995 |
| WO | 9518971 | 7/1995 |
| WO | 9520973 | 8/1995 |
| WO | 9522058 | 8/1995 |
| WO | 9522625 | 8/1995 |
| WO | 9525177 | 9/1995 |
| WO | 9531210 | 11/1995 |
| WO | 9533846 | 12/1995 |
| WO | 9535278 | 12/1995 |
| WO | 9535505 | 12/1995 |
| WO | 9600148 | 1/1996 |
| WO | 9600378 | 1/1996 |
| WO | 9600391 | 1/1996 |
| WO | 9605214 | 2/1996 |
| WO | 9616333 | 5/1996 |
| WO | 726520 | 8/1996 |
| WO | 9623813 | 8/1996 |
| WO | 9629088 | 9/1996 |
| WO | 9633736 | 10/1996 |
| WO | 9636732 | 11/1996 |
| WO | 9639165 | 12/1996 |
| WO | 9640204 | 12/1996 |
| WO | 9640738 | 12/1996 |
| WO | 9640749 | 12/1996 |
| WO | 9640987 | 12/1996 |
| WO | 9702357 | 1/1997 |
| WO | 9710365 | 3/1997 |
| WO | 9720078 | 6/1997 |
| WO | 9727317 | 7/1997 |
| WO | 9729212 | 8/1997 |
| WO | 9739151 | 10/1997 |
| WO | 9741093 | 11/1997 |
| WO | 9743450 | 11/1997 |
| WO | 9743611 | 11/1997 |
| WO | 9749845 | 12/1997 |
| WO | 9812354 | 3/1998 |
| WO | 9812559 | 3/1998 |
| WO | 9916103 | 4/1998 |
| WO | 9818967 | 5/1998 |
| WO | 9820967 | 5/1998 |
| WO | 9824796 | 6/1998 |
| WO | 9827430 | 6/1998 |
| WO | 9829535 | 7/1998 |
| WO | 9830883 | 7/1998 |
| WO | 9838846 | 9/1998 |
| WO | 9839348 | 9/1998 |
| WO | 9841657 | 9/1998 |
| WO | 9844100 | 10/1998 |
| WO | 9846551 | 10/1998 |
| WO | 9853841 | 12/1998 |
| WO | 9856954 | 12/1998 |
| WO | 9858529 | 12/1998 |
| WO | 9859072 | 12/1998 |
| WO | 9859360 | 12/1998 |
| WO | 9859361 | 12/1998 |
| WO | 9859362 | 12/1998 |
| WO | 9902682 | 1/1999 |
| WO | 9904440 | 1/1999 |
| WO | 9905323 | 2/1999 |
| WO | 9905324 | 2/1999 |
| WO | 9905574 | 2/1999 |
| WO | 9905591 | 2/1999 |
| WO | 9906833 | 2/1999 |
| WO | 9909218 | 2/1999 |
| WO | 9918434 | 4/1999 |
| WO | 9927105 | 6/1999 |
| WO | 9928475 | 6/1999 |
| WO | 9932662 | 7/1999 |
| WO | 9935256 | 7/1999 |
| WO | 9937659 | 7/1999 |
| WO | 9939004 | 8/1999 |
| WO | 9940105 | 8/1999 |
| WO | 9945021 | 9/1999 |
| WO | 9945357 | 9/1999 |
| WO | 9950456 | 10/1999 |
| WO | 9951733 | 10/1999 |
| WO | 9951778 | 10/1999 |
| WO | 9954509 | 10/1999 |
| WO | 9954718 | 10/1999 |
| WO | 9963113 | 12/1999 |
| WO | 9964626 | 12/1999 |
| WO | 9965945 | 12/1999 |
| WO | 0000808 | 1/2000 |
| WO | 0004372 | 1/2000 |
| WO | 0006771 | 2/2000 |
| WO | 0011223 | 3/2000 |
| WO | 0040942 | 7/2000 |
| WO | 0053736 | 9/2000 |
| WO | 0065098 | 11/2000 |

OTHER PUBLICATIONS

Bronk et al., "Fabrication of patterned sensor arrays with arylazides on a polymer-coated imaging optical fiber bundle." *Anal Chem* (1994) 66:3519-3520.

Gautler et al., "Fiber optic biosensor based on luminescence and immobilized enzymes: Microdetermination or sorbitol, ethanol and oxaloacetate." *J Biolum Chemilum* (1990) 5:57-63.

Walt et al., "Self regenerating fiber opic sensors." In *Direct Monitoring of Antigen-Antibody Interactions by Special Interferometry*. ACS Symposium Series (1995) 586:186-196.

Ferguson et al., "A fiber-optic DNA biosensor microarray for the analysis of gene expression." *Nat Biotech* (1996) 14:1681-1684.

* cited by examiner

MICROARRAYS AND THEIR MANUFACTURE BY SLICING

CROSS REFERENCE TO RELATED APPLICATIONS

The instant application is a continuation-in-part of patent application Ser. No. 09/628,339 filed Jul. 28, 2000 now U.S. Pat. No. 6,846,635 which is a continuation-in-part of patent application Ser. No. 09/482,460 filed Jan. 13, 2000 now U.S. Pat. No. 6,713,309 which is a continuation-in-part of application Ser. No. 60/146,653 filed Jul. 30, 1999, the contents of which are incorporated herein in entirety.

FIELD OF THE INVENTION

The instant invention relates to microarrays containing bioreactive molecules, uses thereby and methods for manufacture thereof. The arrays are constructed by sectioning bundles of tubules or rods, each containing unique reactants to produce large numbers of identical arrays.

BACKGROUND OF THE INVENTION

A microarray is essentially a two-dimensional support or sheet wherein different portions or cells (sectors) of the support or sheet carry different biomolecules or elements, such as, nucleotides, polynucleotides, peptides, polypeptides, saccharides or polysaccharides, bound thereto. Microarrays are similar in principle to other solid phase arrays except that assays involving such microarrays are performed on a smaller scale, allowing many assays to be performed in parallel. Microarrays have been used for a number of analytical purposes, typically in the biological sciences.

Biochemical molecules on microarrays have been synthesized directly at or on a particular cell (sector) on the microarray, or preformed molecules have been attached to particular cells (sectors) of the microarray by chemical coupling, adsorption or other means. The number of different cells (sectors) and therefore the number of different biochemical molecules being tested simultaneously on one or more microarrays can range into the thousands. Commercial microarray plate readers typically measure fluorescence in each cell (sector) and can provide data on thousands of reactions simultaneously thereby saving time and labor. A representative example of a patent in the field is U.S. Pat. No. 5,545,531.

Currently, two dimensional arrays of macromolecules are made either by depositing small aliquots on flat surfaces under conditions which allow the macromolecules to bind or be bound to the surface, or the macromolecules may by synthesized on the surface using light-activated or other synthetic reactions. Previous methods also include using printing techniques to produce such arrays. Some methods for producing arrays have been described in "Gene-Expression Micro-Arrays: A New Tool for Genomics", Shalon, D., in *Functional Genomics; Drug Discovery from Gene to Screen*, IBC Library Series, Gilbert, S. R. & Savage, L. M., eds., International Business Communications, Inc., Southboro, Mass., 1997, pp 2.3.1.–2.3.8; "DNA Probe Arrays: Accessing Genetic Diversity", Lipshutz, R. J., in Gilbert, S. R. & Savage, L. M., supra, pp 2.4.1.–2.4.16; "Applications of High-Throughput Cloning of Secreted Proteins and High-Density Oligonucleotide Arrays to Functional Genomics", Langer-Safer, P. R., in Gilbert, S. R. & Savage, L. M., supra; Jordan, B. R., "Large-scale expression measurement by hybridization methods: from high-densities to "DNA chips", J. Biochem. (Tokyo) 124: 251–8, 1998; Hacia, J. G., Brody, L. C. & Collins, F. S., "Applications of DNA chips for genomic analysis", Mol. Psychiatry 3: 483–92, 1998; and Southern, E. M., "DNA chips: Analyzing sequence by hybridization to oligonucleotides on a large scale", Trends in Genetics 12: 110–5, 1996.

Regardless of the technique, each microarray is individually and separately made, typically is used only once and cannot be individually precalibrated and evaluated in advance. Hence, one depends on the reproducibility of the production system to produce error-free arrays. Those factors have contributed to the high cost of currently produced biochips or microarrays, and have discouraged application of the technology to routine clinical use.

For scanning arrays, charged coupled device (CCD) cameras can be used. The cost of those devices has declined steadily, with suitable cameras and software now widely available. Such devices generally detect light sources or light absorbance. In one proposed variation, an array is located at the ends of a bundle of optical fibers with the nucleic acid or antibody/antigen attached to the other end of the optical fiber. Detection of fluorescence then may be performed through the optical fiber, for example, see U.S. Pat. No. 5,837,196.

Fiber optical arrays can be produced in which glass or plastic fibers are aligned in parallel in such a manner that all remain parallel, and an optical image may be transmitted through the array. Parallel arrays also may be made of hollow glass fibers, and the array sectioned normal to the axis of the fibers to produce channel plates used to amplify optical images. Such devices are used for night vision and other optical signal amplification equipment. Channel plates have been adapted to the detection of binding reactions (U.S. Pat. No. 5,843,767, not prior art) with the individual holes being filled after sectioning of the channel plate bundle, and discrete and separate proteins or nucleic acids being immobilized in separate groups of holes.

Hollow porous fibers have been used for dialysis of biological samples, for example, in kidney dialyzers and for water purification. Methods for aligning the fibers in parallel arrays, for impregnating the volume between the fibers with plastic, and for cutting the ends of such arrays have been described (see, for example, U.S. Pat. No. 4,289,623).

Immobilized enzymes have been prepared in fiber form from an emulsion as disclosed, for example, in Italy Pat. No. 836,462. Antibodies and antigens have been incorporated into solid phase fibers as disclosed in U.S. Pat. No. 4,031,201. A large number of other different immobilization techniques are known in the fields of solid phase immunoassays, nucleic acid hybridization assays and immobilized enzymes, see, for example, Hermanson, G. T., *Bioconiugate Techniques*. Academic Press, New York. 1995, 785 pp; Hermanson, G. T., Mallia, A. K. & Smith, P. K. *Immobilized Affinity Ligand Techniques*. Academic Press, New York, 1992, 454 pp; and *Avidin-Biotin Chemistry: A Handbook*. D. Savage, G. Mattson, S. Desai, G. Nielander, S. Morgansen & E. Conklin, Pierce Chemical Company, Rockford Ill., 1992, 467 pp.

Currently available biochips include only one class of immobilized reactant, and perform only one class of reactions. For many types of clinical and other analyses, there is a need for chips that can incorporate reactants immobilized in different ways in one chip.

SUMMARY OF THE INVENTION

The instant invention relates to a method for producing rods or tubules, each containing a different entrapped or attached biological agent of interest; for arranging and keeping the rods or tubules in parallel bundles; optionally, for impregnating or embedding the bundles with a sectionable adhesive material; optionally, for checking that all elements of the bundle maintain a constant arrangement or pattern throughout the length of the bundle after impregnation; for sectioning the bundle to produce large numbers of identical arrays or chips; and for performing a variety of different quantitative biochemical analyses on individual arrays or chips based on, for example, enzymatic activities, immunochemical activities, nucleic acid hybridization and small molecule binding under conditions yielding, for example, fluorescence, optical absorbance or chemiluminescence signals, for acquiring images of the signals which can be processed electronically and compared to produce clinically and experimentally useful data.

In a further, the invention relates to long filaments or tubes that contain, are coated with, or have an agent of interest embedded therein, and methods for manufacture thereof.

In another aspect, the invention relates to a device comprising a substrate or solid phase having at least two (2) opposing major surfaces and multiple discrete channels extending to at least the two opposing surfaces. Further, the channels may comprise a first and second binding reagent immobilized on the walls of a first and second group of channels. In a related aspect, the binding reagents may or may not be identical.

In a further aspect, the invention relates to a device comprising a rigid support that is integral to a substrate or solid phase or is bonded to a substrate or solid phase. In a related aspect, the substrate or solid phase has a flat surface and a plurality of structures projecting away from the plane of the solid phase. Moreover, such structures may be permeable or impermeable to fluids.

The invention also relates to methods for arranging the fibers to form bundles in which the position of each fiber relative to all others is retained throughout the bundle length.

The invention further relates to means and methods for attaching or gluing all of the fibers together over the entire length thereof.

In a related aspect, the invention relates to the preparation of microarrays wherein the elongated filaments or tubes are bundled together and cut transversely many times at short intervals to yield cross sectional slices thereof to form microarrays and a microarray so prepared.

A further aspect of the invention is the inclusion of markers which are either integral with the tubes or fibers or are contained in the media contained in hollow fibers which allow the fibers to be distinguished along the entire length thereof.

An additional aspect of the invention includes means for illuminating fibers individually at one end of a bundle, and identifying the other end by photoelectric means to confirm the integrity of the fiber arrangement.

In another aspect, the instant invention relates to forming a fiber containing an agent of interest, or means for immobilizing one or a class of agents of interest thereto.

In an additional aspect, the invention relates to means for embedding or attaching whole or fragments of biological cells, tissues or infectious agents to fibers or tubules in such a manner that the biologicals are exposed on the cut end of each fiber of tubule.

In another aspect of the invention, the array consists of tubules containing gel or other polymerizing materials that adhere to the tubing walls.

In a further aspect of the invention, agents of interest are attached to the polymerizing or suspending medium in the lumen of small tubes.

In yet another aspect of the invention, the agents of interest are attached to particles that are suspended in a polymerizing medium, which suspension is used to fill tubules used to make array bundles and arrays.

The invention further relates to a method for the large scale production of identical flat two-dimensional arrays of immobilized nucleic acid-based agents for use in nucleic acid sequencing, in the analysis of complex mixtures of ribonucleic acids (RNA's) and deoxyribonucleic acids (DNA's), and in the detection and quantification of other analytes including proteins, polysaccharides, organic polymers and low molecular mass analytes, by sectioning long bundles of fibers or tubes containing same.

In a related aspect, the invention relates to exploiting microarrays for mass screening of large numbers of samples from one to a large number of agents of interest.

In another aspect of the instant invention, one may perform quality control assays on each fiber after manufacture, so that only fully functional fibers are included in a fiber bundle.

In a further related aspect, the invention relates to the development of sets of tests on different chips or microarrays done in optionally branching sequence, which reduces the cost, delay and inconvenience of diagnosing human diseases, while providing complex data ordinarily obtained by time-consuming sequential batteries of conventional tests.

In still another aspect, the invention relates to the fabrication of identical arrays that are sufficiently inexpensive to allow several identical arrays to be mounted on the same slide or test strip, and cross-compared for quality control purposes.

In a still further aspect, the invention relates to the incorporation of a non-fluorescent dye or other light absorbing material in the substance of the array to control the depth to which light used to excite fluorescence penetrates the array, thereby controlling the depth to which fluorescence analytes are detected, and insuring that fluorescent analytes which diffuse too deeply into the content of the cells, and therefore do not diffuse out, are not detected.

In another aspect, the invention relates to methods for determining that tubules are completely full of support media, and lack voids or air bubbles.

In a further aspect, the invention relates to methods and apparatus for completely filling small tubes with a supporting medium using hydrostatic force or centrifugal force.

In an additional aspect, the invention relates to the reproducible manufacture of biochips or microarrays for bioanalysis.

In a further aspect, the invention relates to the design and production of arrays, which are specifically designed to detect and diagnose a specific disease.

In yet another aspect, the instant invention relates to multiwell plates and methods for manufacture thereof.

In yet a further aspect, the invention relates to increasing the dynamic range of multiple-parallel assays by providing means for making serial measurements of fluorescence or absorbance over time, and for determining the rate of change of fluorescence or absorbance in each element of the array over time.

It is an additional aspect of the invention to produce biochips that are inexpensive and sufficiently standardized to allow more than one to be used for each analysis, and for controls and standards to be run routinely and simultaneously in parallel. For added quality assurance, sections from different portions of the bundle or different ends may be used. One way of sectioning from different portions of the bundle is to cut or bend the bundle in the middle and align the two halves to form a single larger bundle thereby producing a section where each fiber is represented twice.

In a further aspect, the invention relates to the production of chips in which the array elements or cells (sectors) may differ from one another in the composition of the tubes, supporting medium, immobilization surface, or the class of agent of interest may be different in different cells (sectors).

In an additional aspect, the invention relates to the production of chips in which different types of reactions may be carried out at the surface of each cell (sector) of the array, with the reactions including immunological, enzymatic or hybridization reactions.

A further aspect of this invention relates to the production of subarrays of fibers or tubules adhering together to form one-dimensional ribbon-like arrays which may be separately stored. The "ribbons" may be subject to quality control analysis before being assembled into two-dimensional arrays. Different one-dimensional arrays may be used to assemble different arrays, thus providing the option of producing custom-made arrays to meet specific research and clinical requirements.

The invention further relates to the development of multiple parallel chip-based methods involving continuously increasing temperature such that temperature sensitive reactions may be carried out at physiological temperatures, followed by an increase in temperature to allow hybridization reactions to occur.

In a still further aspect, the invention relates to preparing libraries of compounds with each fiber containing one of the compounds. The array may be used to screen simultaneously all of the compounds for a particular chemical or biological activity.

DETAILED DESCRIPTION OF THE INVENTION

Figure 1:
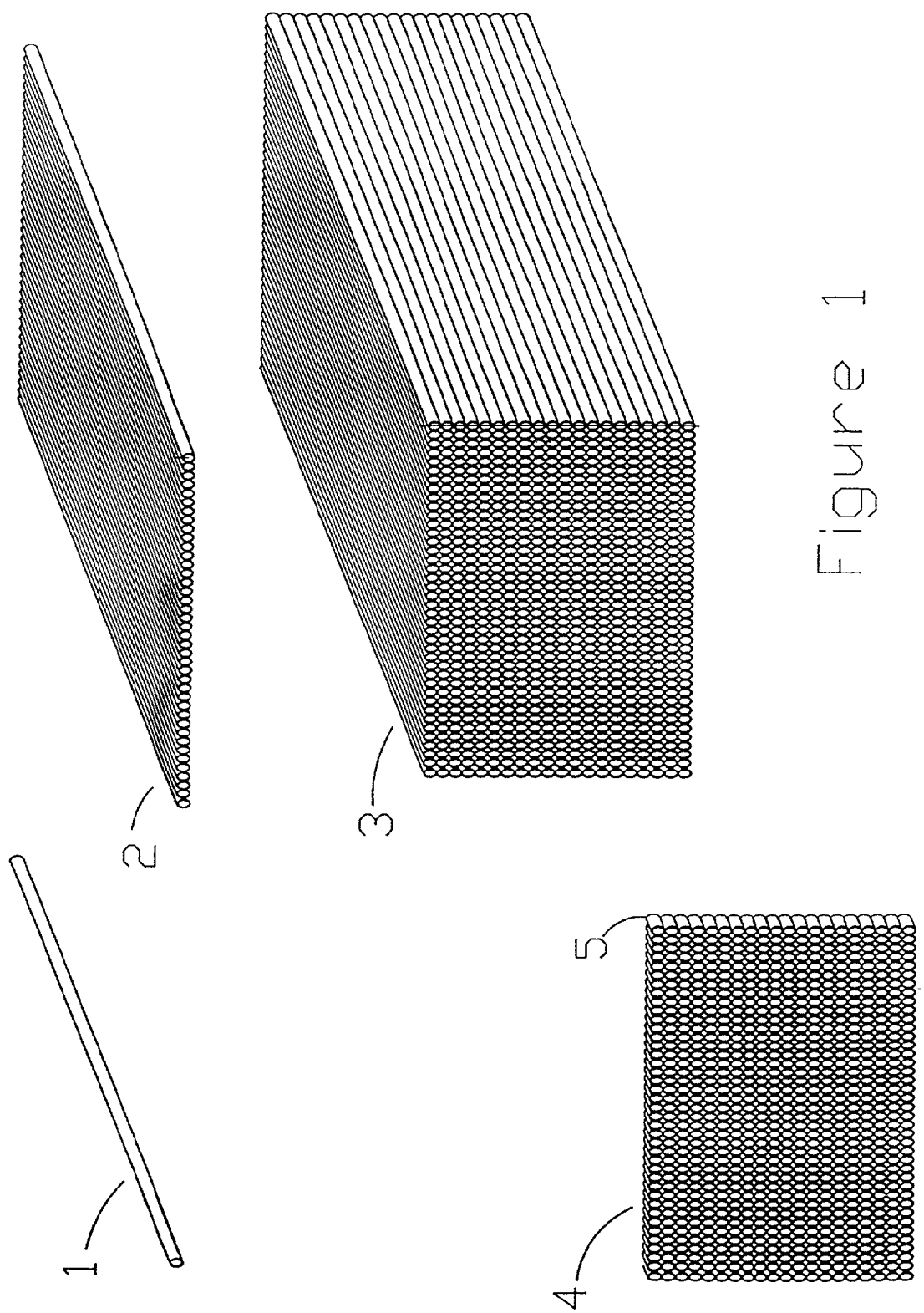
FIG. 1 is a schematic of intermediate products in the process for producing microarrays.
Figure 2:
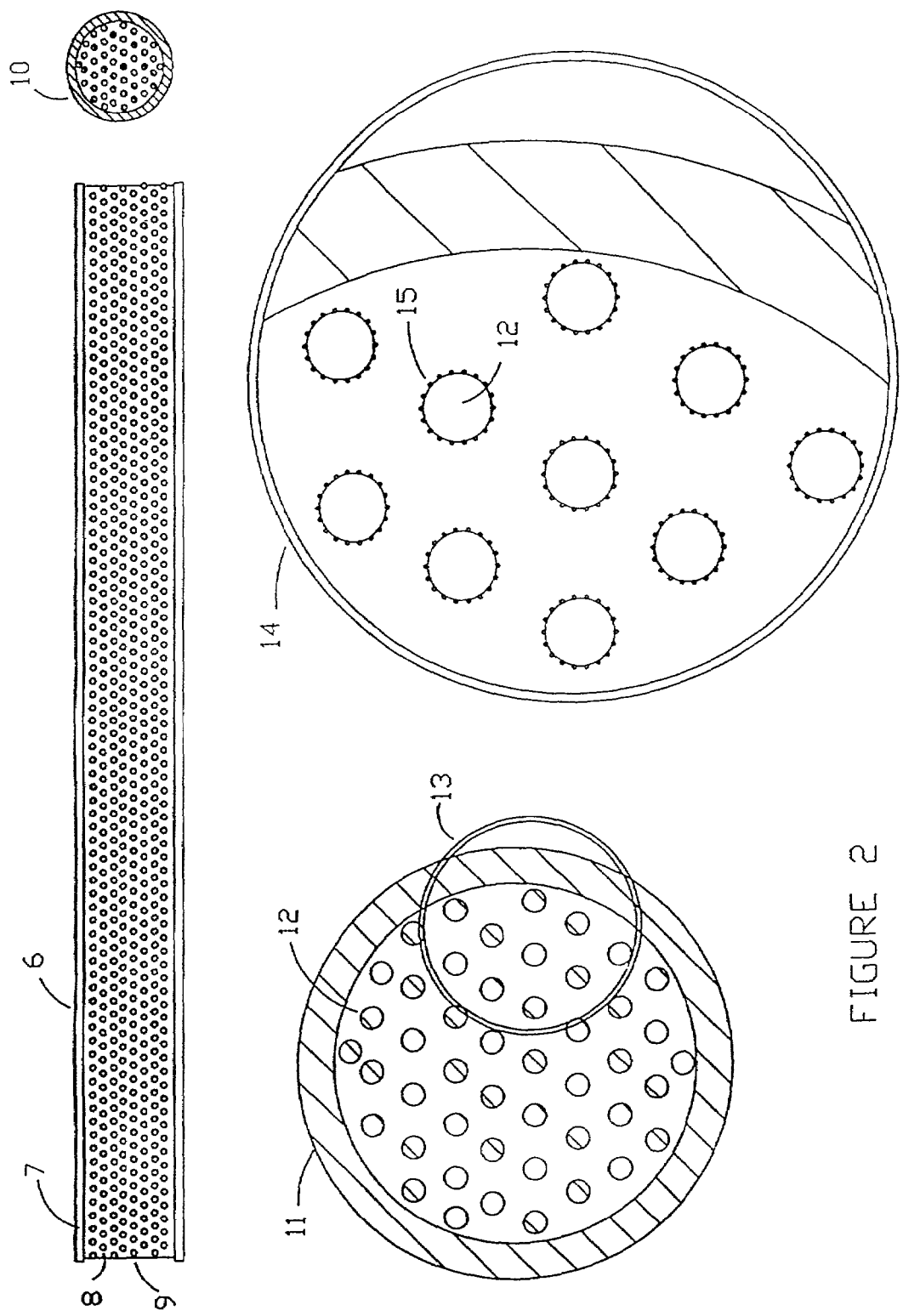
FIG. 2 is a schematic of an individual tubule containing beads with immobilized ligands embedded in a gel.

The terms "binding component", "molecule of interest", "agent of interest", "ligand" or "receptor" may be any of a large number of different molecules, biological cells or aggregates, and the terms are used interchangeably. Each binding component is immobilized at a cell, sector, site or element of the array and binds to an analyte being detected.

Therefore, the location of an element or cell containing a particular binding component determines what analyte will be bound. Proteins, polypeptides, peptides, nucleic acids (nucleotides, oligonucleotides and polynucleotides), antibodies, ligands, saccharides, polysaccharides, microorganisms such as bacteria, fungi and viruses, receptors, antibiotics, test compounds (particularly those produced by combinatorial chemistry), plant and animal cells, organdies or fractions of each and other biological entities may each be a binding component if immobilized on the chip. Each, in turn, also may be considered as analytes if same bind to a binding component on a chip.

When a molecule of interest has a high molecular weight, it is referred to as a "macromolecule". In terms of some biopolymers, the high molecular weight refers to greater than 100 amino acids, nucleotides or sugar molecules long.

The term "bind" includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measuring. The "binding" interaction may be brief as in the situation where binding causes a chemical reaction to occur. That is typical when the binding component is an enzyme and the analyte is a substrate for the enzyme. Reactions resulting from contact between the binding agent and the analyte are also within the definition of binding for the purposes of the present invention.

The term "cells", "sectors", "sites" or "elements" in the instant application refers to a unit component of an array identified by a unique address, which generally differs from other cells, sectors, sites or elements by content as well as location. Biological cells generally are referred to by type, e.g. microorganisms, animal and plant cells.

The term "fibers" includes both filaments and hollow capillary structures. Filaments or rods may be solid strands of monolithic, porous or composite forms, or aggregate forms. Pluralities, typically a large number, of fibers are bound adjacent to each other in ribbons or bundles to form a "fiber bundle." A fiber bundle may constitute a portion of the actual bundle being used such as ribbon. The cross-section of the fibers may be of any shape, such as round, triangular, square, rectangular or polygonal.

The term "surface" refers to the exterior boundaries of an object.

The term "particle" includes a large number of insoluble materials of any configuration, including spherical, thread-like, brush-like and many irregular shapes. Particles are frequently porous with regular or random channels inside. Examples include silica, cellulose, Sepharose beads, polystyrene (solid, porous and derivitized) beads, controlled-pore glass, gel beads, sols, biological cells, subcellular particles, microorganisms (protozoans, bacteria, yeast, viruses, etc.) micelles, liposomes, cyclodextrins, two phase systems (e.g. agarose beads in wax) etc. and other structures which entrap or encapsulate a material. Particularly preferred are recombinant hosts and viruses that express the protein of interest. Even certain high molecular weight materials, such as, polymers and complexes, may serve as immobilizing structures that would constitute a "particle".

The term "sintering" refers to the adhesion of the surfaces of the fibers without actually melting the whole fiber. Sintering may be chemical or thermal and may even involve a self adhesive component that may be activatable.

The terms "arrays" and "microarrays" are used somewhat interchangeably differing only in general size. The instant invention involves the same methods for making and using either. Each array typically contains many cells (typically 100–1,000,000+) wherein each cell is at a known location and contains a specific component of interest. Each array therefore contains numerous different components of interest.

In a related aspect, "device" is used to describe both arrays and microarrays, where the array or microarray may comprise other defined components including surfaces and points of contact between reagents.

Further, "substrate" is also a term used to describe surfaces as well as solid phases which may comprise the array, microarray or device.

The instant invention makes microarrays, "chips" or "biochips" by sectioning bundles of small plastic rods, fibers, tubes or tubules containing immobilized binding component, including biological molecules and entities such as nucleic acid fragments, nucleotides, antigens, antibodies, proteins, peptides, carbohydrates, ligands, receptors, drug targets, biological cells or subfractions thereof (e.g. ground-up cells, organelles, solvent extract etc.), infectious agents or subfractions thereof, drugs, toxic agents or natural products. Embedding media may be, in the instant invention, polymerized or solidified in small tubes, or may be cast into rods or sheets.

The tubes may be of material such as glass, metal, ceramic or plastic. The immobilized binding components, e.g. nucleic acids, proteins, cells etc., may be coated on the inside or outside of the microtubes, contained in a gel in the microtubes, or attached to or embedded in small particles or beads which fill the tubes. The particles or beads may be a component of a gelling material or can be separate components such as latex beads made of a variety of synthetic plastics (polystyrene etc.). When the individual fibers are solid rods or filaments, the agent of interest is incorporated on or in the plastic before the filament is cast, extruded or pulled through a die. Each section cut constitutes a microarray for use in various binding assays.

A key aspect of the invention, which provides an economic advantage, is that the fibers or tubules are prepared using only methods providing a functionality stable to long term storage are used. Unlike other methods involving protein containing liquids which must be prepared fresh each time, immobilized proteins in relatively dry form remain stable for great lengths of time, often without refrigeration.

The preparation of each component of a future microarray separately in/on a fiber permits one to assay for and evaluate the functionality or reactivity of each component before being incorporated in an array. Both the spotting technique and the in situ synthesis technique do not permit testing before completion. Furthermore, quality control checks can sample only a small portion of such microarrays, which is unlike the instant invention where each fiber may be tested.

Various aspects of the invention are illustrated in FIGS. 1–7.

General principles are illustrated in FIG. 1 where rod or tube 1 incorporates an agent of interest. The rods or tubes may be bonded into a flat parallel array 2, and multiple flat arrays then are bonded into the multiple parallel bundle 3. Alternatively, the bundle 3 may be constructed in one step from a series of rods 1. The end of bundle 3 is cut or sectioned to yield the final array 4 that contains one small section 5 of each rod or tube in the entire bundle. By making a long bundle 3, and cutting very small sections 4, a very large number of identical arrays or chips are formed. For example, if bundle 3 is a meter long, and the sections are 10 microns thick, 100,000 identical chips may be produced.

In the case of hollow glass fibers, such as those in channel plates, the hollow fibers may be filled with gels or particles including immobilized reactants, and the entire bundle sawed into arrays.

The rods or tubules comprising the sectioned bundle fall into at least eight classes, with subdivisions of each.

A first class is composed of solid rods or filaments with the immobilized binding component being part of the composition of the rod or filament. The agent of interest in the instant invention may comprise a very broad range of chemicals, complexes, tissues, biological cells or fractions thereof. Nucleic acids, sugars, proteins, which may be modified or coated with detergents to enhance solubility in organic solvents, and a wide range of organic compounds can be incorporated into polymerizing mixtures such as those used to produce plastics. Oligonucleotides and nucleic acids are soluble in methylene chloride, for example, and hence may be included in acrylics during polymerization.

A number of polymerizing embedding agents have been developed for histological and histochemical studies, some of which are listed in Table 1, together with data on composition, curing temperature, solvent used and viscosity.

TABLE I

| RESIN* | TYPE | CURE TEMP. | SOLVENT | VISCOSITY |
|---|---|---|---|---|
| Durcupan | — | 40° C. | Water | Medium |
| Nanoplast | Melamine | 60° C. | Water | Low |
| Quetol 651 | Epoxy | 60° C. | Water | Low |
| London Resin Gold | Acrylic, UV Curing | −25° C. | Water, EtOH | Low |
| Lowicryl K4M Polar | Acrylic, UV Curing | −35° C. | Water, EtOH | Low |
| Lowicryl Monostep K4Mpolar | Acrylic, UV Curing | −35° C. | Water, EtOH | Low |
| Lowicryl K11 Polar | Acrylic UV Curing | −60° C. | EtOH | Low |
| JB-4 | GMA | RT | Water | Low |
| JB-4 Plus | Methacrylate | RT | Water | Low |
| ImmunoBed | GMA | RT | Water | Low |
| PolyFreeze | Polyol | −15° C. | Water | Low |

*Available from Polysciences

Other methods for impregnating a solid fiber include mobilizing the agent of interest through the matrix of the solid fiber using an electromotive force.

In one embodiment, the microarrays are produced by diffusion and entrapment after polymerization of the strands. An element of a microarray is formed by preforming a polymeric strand, then incorporating a biological target molecule into the strand by a method including, but not limited to, diffusion from a solution containing the biological target molecule. Such a method of incorporating labile biological target molecules into polymeric avoids harsh conditions of polymerization, such as heat, presence of free radicals etc. that might alter a biological target molecule. Further, such a method envisages entrapping the biological target molecule within the polymeric strand while concomitantly preventing subsequent diffusion of the biological target molecule out of the strand. For example, a polymeric strand of material can be prepared from a material such as, but not limited to, ImmunoBed (Polysciences, Warrington, Pa.), polyacrylamide, agarose etc. Further, a mixture of monomeric substances can be mixed with an entrapping agent, such as but not limited to, protein-biotin complexes.

The mixture can then be introduced into tubing (e.g., polyethylene) and allowed to polymerize. A strand thus formed can be extruded from the tubing mold and placed in a solution containing a biological target molecule of interest. In one embodiment, the biological target molecule of interest will be conjugated to a biotin-binding protein such as streptavidin. However, other binding pairs, which are known in the art, are also envisaged for this purpose (e.g., antibody-antigen, nucleic acid-nucleic acid, protein-protein, protein-nucleic acid, receptor-ligand, lectin-antibody, cell-cell, etc). The strand is allowed to remain in contact with the solution for a period of time, at a temperature that is consistent with maintenance of biological activity. In one embodiment, the temperature range is between about 4° C. to about 70° C., more preferably about 4° C. to about 40° C. The temperature is chosen based on the solidifying properties of the matrix and the thermolabile properties of the agent of interest.

The period of time of contact between the strand and the solution for optimal incorporation of the biological target molecule into the strand will depend on many factors, including, but not limited to, porosity of the strand, molecular size of the biological target molecule, concentration of the biological target molecule, temperature etc. After the strand is loaded with biological target molecule, the strand is washed with buffer and aligned with other strands to form an array.

A second class of fibers is not homogeneous and the polymerizing or gelling material also may contain solid structural elements such as filaments, branched elements etc., to further strengthen the gel and also may provide attachment sites for the agent of interest. Thus, the added components serve to strengthen the gel and may provide attachment sites for inclusions including dendrimer branched polynucleic acids, branched or crosslinked polymeric materials, metal or glass fibers. Threads, yarn-like configurations and brush-like configurations of structural elements may be cast into the length of the fiber to provide strength and to allow the fiber to be handled or dried more easily. The structural elements may serve as the immobilizing component in the fiber for a desired binding component.

Thus, it is technically feasible to produce long fibers of acrylic or other plastics each containing a different agent of interest using currently available extrusion technology in the instant invention. The cut end of the fibers may be treated briefly with dilute solvents to expose active groups.

A third class of fibers includes extruded or cast plastic, which includes a second phase. The second phase may be in the form of, for example, hydrocarbon, aqueous or fluorocarbon microdroplets, particles of sugars or other water soluble materials, or inorganic particles such as calcium carbonate particles, which can be dissolved in dilute acid to reveal active groups. Brief exposure of the cut surface of a chip to a solvent will dissolve some of the inclusions, increasing the surface area of the support plastic containing the agents of interest. In another embodiment, the material between the fibers can be removed, increasing the available surface on the exterior of the fiber for interaction between target and agent of interest.

In a related aspect, each fiber may contain two or more materials possessing different properties such as, but not limited to, polyethylene fiber and an acrylamide gel with the protein. The materials may be attached by a cyanoacrylate adhesive. Likewise, for the glue holding the fibers together, the glue may be made of a different material. In a related aspect, such mixed fibers may comprise the same or different protein immobilized in a matrix comprising one or more heterogeneous materials.

Solid plastics also can be prepared which incorporate polystyrene latex or other plastic particles to which proteins or nucleic acids are attached. Conditions can be arranged such that the supporting plastic is eroded to a depth of a few microns to reveal active subparticle surfaces, and do not dissolve the supporting plastic latex beads. For example, proteins derivatized with fluorinated groups attach strongly to Teflon® microparticles. Such derivatized Teflon® particles in, for example, an acrylic plastic or other suitable embedding medium, can be partially exposed at the plastic surface by a dilute acrylic solvent, composed, for example, of methylene chloride and ethyl alcohol. Alternatively, the particles may be embedded in a porous matrix.

The beads to which agents of interest are attached may be porous gel beads used in chromatography such as Sephadex, Biogels and others, or solid beads such as are used in chromatography. A variety of methods for derivitizing such support structures and for attaching polypeptides, proteins, nucleic acids, polynucleotides, saccharides, polysaccharides and small molecules thereto have been developed and are known to those skilled in the arts. The construction of such tubules is illustrated in FIG. 2 where tubule 6 is comprised of tube 7 containing gel 8 which supports particles 9. An end view 10, and enlarged view 11 of the tubule shows exposed particles 12 at the cut end. Area 13 is shown additionally enlarged at 14 to illustrate the presence of immobilized reactants 15 on the surface of the exposed particles 12.

Note that all rods described can be cast with a string or thread through the center thereof to increase strength, and to make the rods easier to handle.

A fourth class of fibers is prepared by sintering glass or plastic beads to form a porous material with a high surface to mass ratio. Such material is conventionally made from glass, polytetrafluoroethylene (PTFE) (Teflon®), Teflon® AF, polyethylene, polypropylene, can be manufactured from polystyrene and from a variety of other plastics. Heat, pressure or exposure to solvent vapors can sinter plastics. The sintered material can be derivatized in sheets or in cut rods. Polystyrene is convenient from the point of view of coupling agents of interest thereto. For polystyrene derivatization, methods that allow attachment of proteins by the amino groups, carboxyl groups, or sulfhydryl groups thereof, have been described. Teflon® can be activated using solutions of metallic sodium in an organic solvent producing groups to which other plastics will adhere, and then may be derivatized. Polyethylene and polystyrene can be activated by corona plasma discharge or by electron beam radiation. An advantageous approach is to make sintered composites of polystyrene and polyethylene. Nylon beads also can be sintered and derivatized. Other sintered materials are known or are under development, many of which will find application here.

Molecules of interest may be attached to the solid materials either before or after sintering. For attachment of the ligands, the rods may be soaked in tubes containing the substance to be attached or the rods may be coiled up inside a hollow bowl centrifuge rotor having the general configuration of a zonal rotor (see Anderson, N. G., Natl. Cancer Inst. Monograph No. 21), but which may be centrifugally drained. The solution of the substance to be attached then is centrifuged first into the sintered mass, and then out of it, followed by washing as necessary. The sintered rods then may be dried, coated with a suitable adhesive, assembled into a bundle and sectioned.

Alternatively, the beads with agents and items of interest attached thereto may be extruded under pressure to form rods that then may be sintered together. The assembled tubes may be held together with a variety of cements or polymerizeable plastics. The outside of the tubes may be altered or treated so that cements or polymerizeable plastics will adhere thereto.

Figure 3:
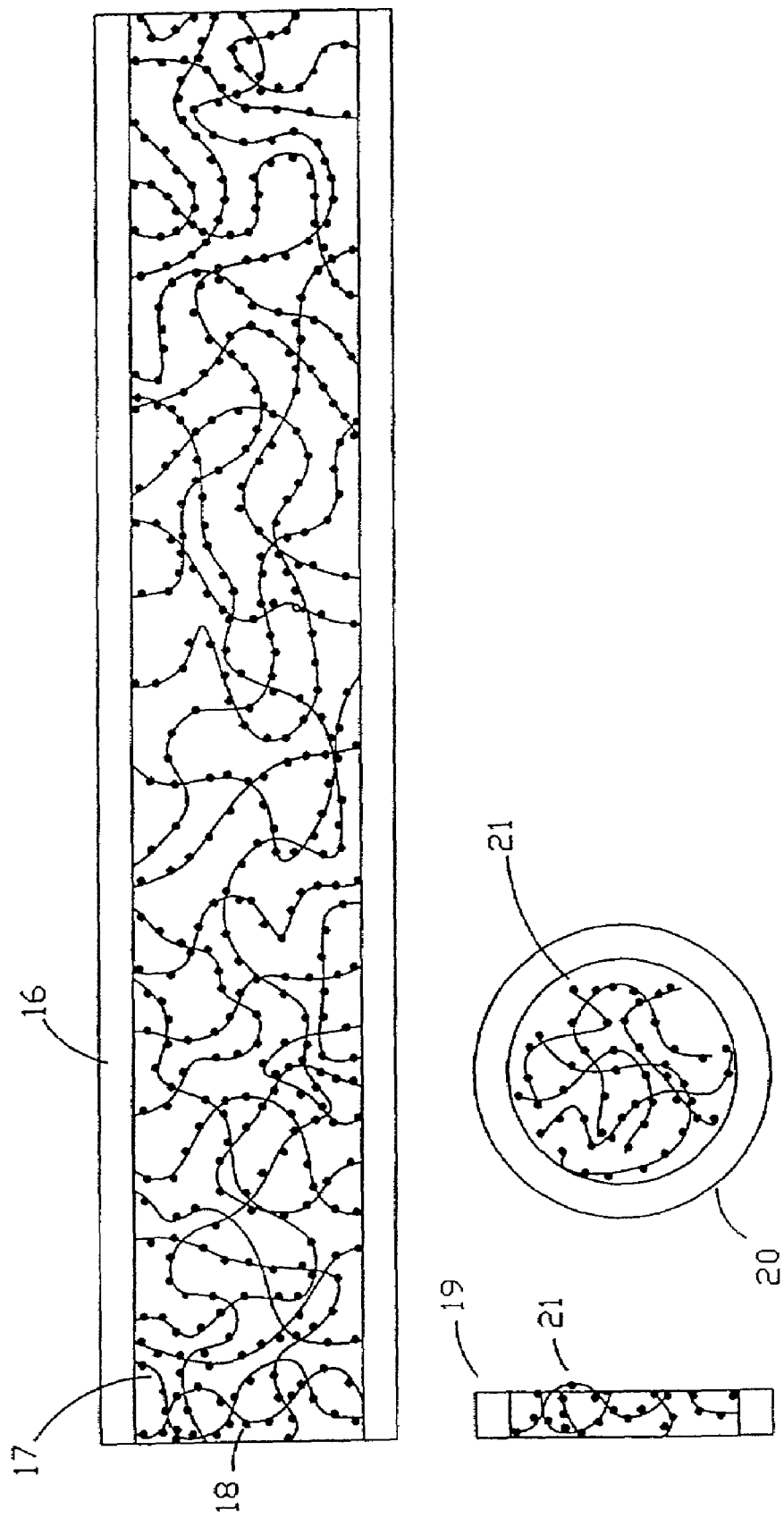
FIG. 3 is a schematic of an individual tubule containing a gel with ligands attached to the gel.

A fifth class of fibers is comprised of hollow impermeable tubules typically formed from plastics including, but not limited to, polyethylene, polypropylene, Teflon® or polyvinyl chloride, and is filled completely with a gel or other polymerizing material to which agents of interest are attached directly. The external surfaces of the tubes may be modified chemically or physically to accept adhesives used to bind the bundled tubes together. The internal surface also may be modified so that the gel or polymerizing mixture introduced into the tubes will adhere, preferably by covalent attachment. Acrylamide derivatives may be linked to the wall to make an acrylamide gel adhere, while gelatin, agar, or agarose derivatives may be attached similarly to link with the respective gels. Methods for linking agents of interest, such as, proteins and nucleic acids, to linear acrylamide, gelatin and agarose are well known, and the derivatized molecules can be incorporated into the gels used for casting. Acrylamide can be made to gel at room temperature either chemically or using photoactivation, while low temperature-gelling Sepharose is available. Gelatin sets slowly and at temperatures below ambient. The polymers used to fill the tubes are typically homogeneous, but may contain agents of interest, which become attached to the polymerizing medium. Examples include covalent attachment of proteins to short acrylamide chains that become incorporated into acrylamide gels and proteins covalently linked to gelatin. Thus, gels are available or can be produced which contain labile biomolecules without exposing them to denaturing temperatures. The structure of such tubes is illustrated in FIG. 3 where tube 16 is filled with a cross-linked gel 17 to which are attached agents of interest 18. A side view 19 and end view 21 of a sectioned tube illustrates the availability of immobilized agents 21.

Arrays prepared using hollow fibers may have the interior of the fibers coated with biomolecules either covalently or in suitable polymer coatings, or in gels before the array is assembled. Isocyanate polymers, such as oxyethylene-based diols or polyols wherein most if not all of the hydroxyl groups thereof carry polyisocyanate groups are suitable. Some such polymers can be comprised of polyurea/urethane polymers. The polymers are well hydrated and fall in the category of hydrogels. Suitable starting materials include triols, such as glycerol, trimethylpropane and triethanolamine, tetrols and polyethylene glycols. Suitable polyisocyanates include diisocyanates and such. The polyisocyanates can be aromatic, aliphatic or cycloaliphatic. (Braatz et al., U.S. Pat. No. 5,169,720 and Braatz, J. Biomaterials Applications 9:71–96 (1994)). Alternatively, a bundled array may be positioned so that individual hollow fibers may be filled with biopolymers in solutions that gel prior to sectioning.

Figure 4:
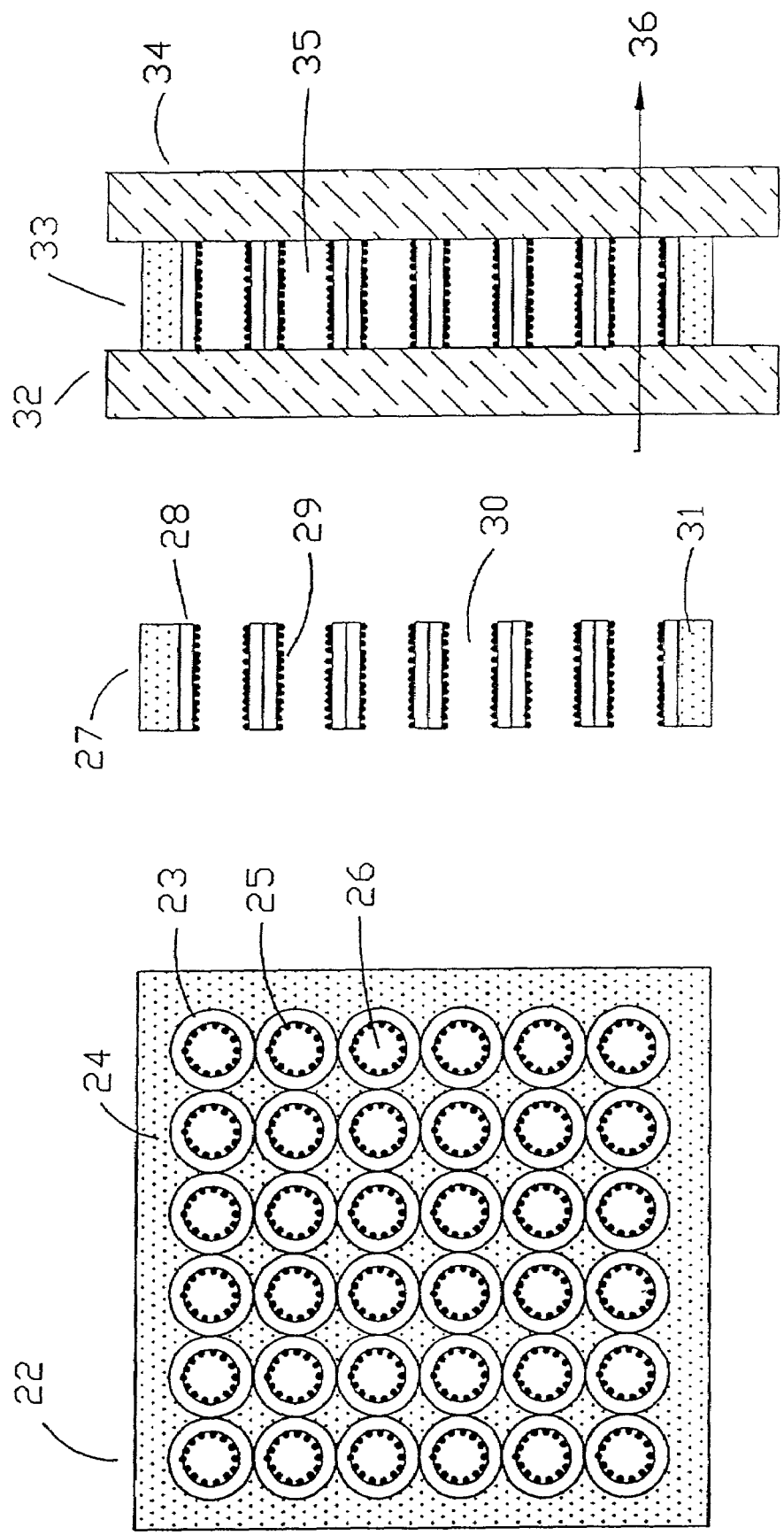
FIG. 4 is a schematic of an array with ligands attached to the inner walls of cells, and with means for closing off one surface of the array to form a set of microwells.

A sixth class of fibers or tubes includes empty impermeable tubes with molecules of interest attached to the inner surface, but otherwise empty or made empty. As illustrated in FIG. 4, the sectioned chip 22 is comprised of sectioned plastic tubes 23 embedded in supporting plastic 24, with the agent of interest 25 attached to the inner walls of the tubes, leaving the center 26 open. The result 27, seen in side section, has sectioned plastic tube 23, immobilized agent 25, yielding open holes 26, and all held together by supporting material 24. The chips may be considered as ultramicrotiter plates and may be used for flow through analysis based on, for example, immobilized affinity ligand techniques (Hermanson et al., Immobilized Affinity Ligand Techniques, Academic Press, 1992, p 407), for polymerase chain reaction (PCR) amplification of immobilized oligonucleotides, or for other detection reactions and the like that can be accomplished at that scale, as described, for example, in U.S. Pat. No. 5,843,767. When the tubes are made of Teflon® with the internal or external surfaces treated to become hydrophilic, the cut ends will remain hydrophobic. When a hydrophilic test solution is spread across the surface of the chip, the solution tends to flow into the holes in self-controlling volumetric amounts, and, if the total amount of fluid is controlled properly, tends not to affect adjacent cells. The upper and lower surfaces then can be sealed with a suitable adhesive tape and the whole subjected to reactions, for example, for polymerase chain reaction amplification of DNA. Alternatively the sandwiched structure 32 including chip 33 of FIG. 4 may employ two pieces of material such as glass or quartz 34 to seal the ends of the tubes, creating microchambers 35. Changes in fluorescence or in optical absorbance 36 may be detected in each tubular element through the transparent end windows, and the reaction followed calorimetrically or fluorometrically.

A variety of other reactions may be performed inside the microarray or inside the hollow fiber used to prepare a microarray. For example, a polypeptide, polysaccharide or polynucleotide may be synthesized in situ and/or a library of combinatorial small molecules such as esters, amides, carboxylates etc., prepared. The same reactions, including PCR, may be performed in any of the other types of fibers, including solid fibers if the fibers are sufficiently permeable to the reactants.

In one embodiment, an array device is envisaged comprising a solid phase and impermeable hollow fibers, where the hollow fibers form a multiple channeled surface. Such a surface can comprise multiple and/or groups of channels where the channels are distinguishable by, but not limited to, differences in channel composition. Further, the channels can extend to at least two exterior surfaces of the solid phase. Moreover, the solid phase may be bound to or integral with a rigid solid support. In a preferred embodiment, the rigid support comprises wells for delivering fluids to subsets of channels comprising the solid phase. In a related aspect, the channels comprise immobilized reagents that may be identical for each channel or group of channels or non-identical. In one embodiment, the channels have a range in diameter of between about 1 μm to about 3 μm. In another embodiment, the channels have a range in diameter of between about 0.45 μm to about 5 μm. In a preferred embodiment, the channels have a range in diameter of between about 0.05 μm to about 8 μm. In a more preferred embodiment, the channels have a range in diameter of between about 0.033 μm to about 10 μm.

Further, such a device having discrete channels can have varying cross-sectional areas. In one embodiment, the cross-sectional area of the channels has a range of between about $1 \times 10^{-2}$ μm$^2$ to about 10 μm$^2$. In another embodiment, the cross-sectional area of the channels has a range of between about $1 \times 10^{-3}$ μm$^2$ to about 30 μm$^2$. In a preferred embodiment, the cross-sectional area of the channels has a range of between about $5 \times 10^{-3}$ μm$^2$ to about 60 μm$^2$. In a more preferred embodiment, the cross-sectional area of the channels has a range of between about $8.5 \times 10^{-4}$ μm$^2$ to about 80 μm$^2$.

In a related aspect, the channels can also vary in inner surface area. In a preferred embodiment, the inner surface area of the channels is from about 100 to about 1000 times the cross-sectional area of the group of channels. In one embodiment, the inner surface area of the channels has a range of between about 100 µm² to about 1×10³ µm². In another embodiment, the inner surface area of the channels has a range of between about 50 µm² to about 5×10³ µm². In a preferred embodiment, the inner surface of the channels has a range of between about 10 µm² to about 3×10⁴ µm².

In another related aspect, the groups of channels can have varying areas on the exterior surface of the device. For example, in one embodiment, the channels have areas in the range of between about 2×10³ µm² to about 3×10⁴ µm². In another embodiment, the channels have areas in the range of between about 200 µm² to about 1×10⁵ µm². In a preferred embodiment, the channels have a range of between about 100 µm² to about 3×10⁵ µm². In a more preferred embodiment, the channels have a range of between about 20 µm to about 3×10⁶ µm².

In a further related aspect, the channels can vary in the number of channels per cm² of solid phase surface. For example, in one embodiment, the number of channels per cm² can be between about 600 to about 700. In another embodiment, the number of channels per cm² can be between about 500 to 1000. In a preferred embodiment, the number of channels per cm² can be between about 450 to about 2000. In a more preferred embodiment, the number of channels per cm² can be between about 400 to about 4400.

When hollow, the microarray may have no agent of interest immobilized thereon or therein. In such a situation, one has a very small multiwell plate, a commercial product per se. By placing, with or without immobilization, biological cells in "empty" hollow fibers; one can use the microarray to determine the cellular response to a specific agent. One may even coimmobilize a substrate or reagent with the biological cells to stimulate production of a detectable product when contacted to or to interact with a specific analyte.

For both measuring the effects of a reagent on biological cellular material and a compound, one may coimmobilize the reagent in the same fiber. Particularly preferred is to have the immobilized agent of interest and reagent(s) in a coaxial relationship within the same fiber. The solidifying matrix holding the reagent(s) may be dissolvable, meltable, degradable, or reversible (e.g. alginate with calcium ions or sodium EDTA) to further enhance interaction. As an example, part of a fiber may contain an immobilized antibody in an insoluble polymer such as a polyurethane. In another part of the same fiber, a labeled antigen is held in a water-soluble matrix such as 7% sodium stearate. Upon adding a target sample, potentially containing unlabeled antigens in water, to a sliced bundle microarray of the fiber, the unlabeled target antigens compete for the immobilized antibody with labeled antigens once the soluble matrix has dissolved. Because the microarrays of the present invention are very thin, dissolving of the soluble matrix and free of the reagents is very quick.

Coextrusion and injection of one material inside the mass of a solid are two other preferred methods for ensuring close contact between the reagents and agents of interest.

As an alternative method for arranging to have reagent in close contact to the agent of interest, two different bundle sections are formed. The first consists of immobilized agents of interest. The second consists of corresponding reagents entrapped in a soluble matrix. One section of each are aligned and in contact with each other such that the end of one fiber contacts the end of another fiber. By adhering the two sections to a solid phase, one on top of the other, the dissolving of the soluble matrix necessarily causes the reagent to contact the immobilized reagent of interest. This contact is enhanced by using impermeable walled tubing to make the fibers and by sandwiching the reagent section between an impermeable solid phase and the section with immobilized agent of interest. In such an arrangement, the only way for the reagent to diffuse out of the microarray is to pass through the cell with immobilized agent of interest.

While the usual technique is to place the molecules or biological components inside the fiber before it is cut to form a microarray, it is an embodiment of the instant invention to place the molecules or biological cells inside the hollow fiber after the microarray is formed. One example is the use of such a microarray to clone biological cells, viruses or other particles by adding a dilute suspension to the microarray. Adding many individual agents of interest may be tedious but is an acceptable use. To compensate for potential spillover into adjacent array cells, one may simply leave one or more rows of empty cells between each array cell being "filled" with an agent of interest.

The inside surface of the small tube described may be modified chemically to allow attachment of polynucleotides, polypeptides, polysaccharides or other molecules either directly or through linkers. The molecules attach, thus increasing the number of reactive sites inside the tube. Since DNA and RNA are conventionally synthesized on small polystyrene beads, the most direct approach to a nucleic acid array is to synthesize oligonucleotides on small polystyrene beads, with different batches of beads having different sequences attached, and then to fill small polyethylene, polypropylene, polystyrene or other plastic, metal or ceramic tubes with the beads, packing down to completely fill the tubes. The beads may be kept in place by careful heating thereof to sinter same or residual latex is added to the tubes and dried in place with air pumped through the tube.

In a related aspect, agents of interest can be attached to inner surfaces, such as, but not limited to, hollow fiber channels, by first derivatizing such agents using terminal primary amine groups and reacting the modified agents with an epoxysilane derivatized inner surface. For example, oligonucleotide probes can be attached to channel surfaces through primary amine groups incorporated into the probe prior to immobilization. Such derivatized probes are then reacted with epoxysilane present on the channel surface, which results in immobilization of the probe.

A seventh class of tubes or fibers includes tubules with permeable walls. Methods and procedures for producing hollow selectively permeable fibers for use in kidney dialysis machines and for molecular weight fractionation have been developed (U.S. Pat. No. 4,289,623, U.S. Pat. No. 3,976,576) and are in wide current use. Procedures for embedding such fibers in solid sectionable plastics also have been developed and are used to attach the fibers to tubing at the dialyzer ends.

Permeable hollow fibers may be used in the instant invention in two ways. In the first, the fibers are filled with reactant-carrying gels while already embedded in plastic. By carefully splaying out the fibers going into the cast portion, each tube can be filled selectively as previously described. That technique offers the advantage of producing small arrays quickly, and of developing new assays without having to go through all of the steps required to produce separate hollow fibers, fill same with reactants, arrange same in arrays and infiltrate same with the supporting plastic.

The second method of use involves filling the hollow fibers before being embedded in plastic. Techniques have been developed for controlling the wall permeability of permeable tubes. That allows the influx and outflux of monomers and gelling agents during gelation to be controlled, and for dialyzable agents to be removed after gelling. For example, acrylamide gels may be produced from acrylamide and bisacrylamide by cross-linking with ultraviolet light in the presence of riboflavin. That technique is preferred when the specific binding component is heat sensitive or sensitive to other chemicals. The catalyst, which would interfere with subsequent fluorescence measurements, can be removed by dialysis through the tubing wall after polymerization.

Another gelling material is an isocyanate-containing prepolymer that polymerizes on contact with water and generates only carbon dioxide as a byproduct of polymerization. The binding component may be incorporated onto solid phase(s) first or otherwise placed in the fiber, which then is polymerized and/or dried to incorporate the binding component to be used on hydration of the gel.

Permeable supporting tubing also allows the gel inside a tube to be infiltrated with substances that render the reactants more stable, increase the physical strength of the gel and facilitate sectioning. For example, sugars such as lactose, trehalose, glycerol, fructose and other polyhydric alcohols may be introduced to stabilize proteins and to add solids to the gels to assist in sectioning. The additives may be removed partially from the exposed surface of the chip during use to make buried reactive groups available. Additives diffusing into the gels also may be used to increase the strength and volume of a gel after it has been dried.

Also, when a particle containing the ligand or receptor is embedded in a fiber, the embedding medium may be soluble or meltable so as to be removable after the microarray is formed. By removing the embedding medium, more active sites on the particle are exposed for binding. That variation is suitable when the particle is actually microfibers or microbrushes of microfilaments having the immobilized ligands or receptors thereon similar to the cross-linked polymers of (17) in FIG. 3.

Once the tubes are filled with the respective gels and reagents, the outside of the tubes is cleaned, may be treated with reagents to increase the adherence of the infiltrating supporting plastic and then bundled to produce the product for sectioning.

An eighth class of tubes or fibers includes those synthesized by cleaving from a larger block, preferably a disk. The fiber material containing the molecule of interest first is cast as a disk and then a long fiber is peeled from the circumference of a rotating disk. That technology is essentially the same as a smaller version of producing wood veneers where the veneer is peeled from a rotating log. The technique has certain space and handling advantages over a long thin fiber. Such a disk also is more easily stored, particularly when active components therein require maintenance under certain conditions, e.g. freezing, submergence in buffer, in the dark etc.

Arrays or parallel fibers may be attached together by many techniques. A preferred one is by vapor sintering. The vapor, perhaps a hot solvent, is allowed to interact with the array for a specified period of time and then is removed by evacuation. In heat sintering, the array is placed under lateral compression and the array heated to the softening point of the plastic. Another means is the use of low melting point metals, such as gallium. By low melting point is meant temperatures at or about physiologic temperature of the binding component.

A variety of histological embedding media has been developed that preserves biological molecules in reactive form. For example, Durcupan, Nanoplast and Quetrol 651 can be cured by very mild heating; JB-4 and Immunobed can be polymerized at room temperature; and the water soluble acrylic polymers, London Resin Gold and Lowicryl, polymerize at below freezing temperatures by ultraviolet light (all are available from Polysciences Inc.). Conventional embedding media use solvents and waxes, and the waxes must be at least partially removed before analysis.

Optionally, use of materials that change the physical dimensions of the fibers or chips under various conditions is also envisaged. In one aspect, the use of such materials can afford the use of larger materials that can be made smaller. For example, such a material would include, but not limited to, heat shrink plastics. A fiber made of such a material could be used to make sections made smaller by heating before or after attachment to a solid phase. In one embodiment, the sliced chip may be made as a "macro" array then shrunk down to a "micro" array. In another embodiment, once heat shrunk (or chemically shrunk as dried or a hydrophilic gel put in a hydrophobic organic solution or vice versa or strong ionic strength solution etc.), the slice may be thicker but have a smaller diameter. In a related aspect, because some of the temperatures required to heat shrink some plastics may denature some proteins, the invention may be used for, but not limited to, microarrays of peptides, oligonucleotides, DNA and combinatorial compounds. In a one embodiment, slow heating is used so that the sliced chip does not crumple into a ball. In a preferred embodiment, the heat shrink plastic has good shrink properties at low temperature (for example, see Paleari et al., U.S. Pat. No. 6,063,417).

In another embodiment, the sliced chips are prepared from dehydrated or shrunken fibers. When such dehydrated or shrunken slices are placed in water (or other solvents), the slice absorbs the water and expands. In a related embodiment, the material surrounding the fiber or part of the fiber is unaffected and the swollen material will protrude making a raised pad. For example, a polyacrylamide gel may be surrounded by opaque polypropylene (carbon black pigment) and the clear polyacrylamide may form a curved surface. In a preferred embodiment such a surface may act as a lens for, but not limited to, fluorescence, light scattering, chemo- or electroluminescence, color formation and stain detection. In a related aspect, to control the amount of dryness to a desirable level for storage, the sliced chip may be placed in a moisture tight container, perhaps with a desiccant. Alternatively, glycerol, humectants or lubricant may be added so that the sliced chip will maintain flexibility. Such substances may be removed before use.

In an alternate embodiment, porous chips are placed on a porous solid support. In a preferred embodiment, agents of interest or binding partners are forced through the porous array by flow, resulting in diffusion distances in the flow through array in the nm range, reducing rate limiting diffusion/hybridization incubation times.

Embedding and sectioning methods therefore are available to identify and localize specific biological molecules. In the case of nucleic acids, specific nucleic acid targets can be detected by, for example, in situ hybridization and amplification of specific sequences by the polymerase chain reaction (PCR) and other nucleic acid amplification techniques (LCR, RCA, SDA etc).

The method of embedding is one that preserves the desired characteristic or characteristics of the binding component in a biological cell. Thus, if antibodies were immobilized in a cell and it is the antigen-binding specificity of the antibody that is desired, the immobilization method will be one which retains the antigen-binding ability of the antibodies. The method and means of attaching the fibers to form the array are also ones, which retain the antigen-binding ability of the antibodies.

Similarly, if the cells contain candidate molecules for binding to a hormone receptor, the immobilizing and attaching method and means are those that retain the configuration of the candidate molecules that allows recognition and binding by the hormone receptor.

In addition, many protein or carbohydrate antigens may be detected using immunological reagents. Detection is generally by incorporation of a fluorescent dye into the analyte or into the second layer of a sandwich assay, or by coupling an enzyme to an analyte or a second or third layer of a sandwich assay that produces an insoluble dye, which may be fluorescent.

Some solid phase surfaces may be used directly to immobilize reactants; others must be modified to allow such additions. Antibodies will adhere to clean polystyrene surfaces, as will many other proteins (Van Oss, C. J., & Singer, J. M. The binding of immune globulins and other proteins by polystyrene latex particles. J. Reticuloendothelial Society 3: 29040, 1966.) Polystyrene, either in the form of microtiter plates or beads, has been modified to bind biological molecules, such as, polynucleotides, polypeptides and polysaccharides. Perfluorocarbon (such as fluorocarbon polymers known as Teflon®), including polytetrafluoroethylene (PTFE), polyvinylfluoride, polyvinylidene difluoride and perfluorodecalin, surfaces bind proteins or other biological molecules (U.S. Pat. No. 5,270,193). Such surfaces can be made to include fluorinated surfactants, which may render the surface hydrophilic, or positively or negatively charged. Glass, including controlled pore glass, may be modified to allow covalent attachment of antibodies, antigens, polysaccharides, polynucleotides, nucleic acids and the like. Plastic surfaces may be modified non-specifically using corona plasma discharge or electron beam radiation and then may be coated with a variety of coatings or adhesives to which macromolecules may be attached. More specific covalent attachment of biological molecules may be achieved by a variety of modifications, which attach reactive groups to polystyrene, or acrylic surfaces, which groups, with or without extending linkers, then will couple under mild conditions to the biopolymers. In a related aspect, the solid phase may be made from glass or silicone, including, but not limited to, nanochannel glass and oriented array microporous silicon.

A variety of chromatographic media also has been adapted to support immobilized bioreactants. Such media include soft gel beads, generally composed of acrylamide, agarose, Sepharose, which may be chemically cross-linked, and less compressible beads designed for high-pressure chromatography. A natural product useful as an immobilization support is cellulose, which is readily available in powdered form. The supports may be modified chemically to allow covalent bioreactant attachment, or may be purchased in modified form ready for attachment.

Long DNA or RNA molecules may be immobilized by being polymerized in a gel and are retained purely by physical entanglement. An example is the retention of DNA in agar or acrylamide gels. In addition, other biological molecules, such as polypeptides, proteins, polysaccharides or nucleic acids may be linked covalently to long polymers so that, when embedded in a gel, diffusion does not occur and the biological molecule remains available for reaction with soluble reactants. Examples include the attachment of proteins or nucleic acids to polyethylene glycol (so-called PEGylation) or to linear acrylamide chains.

In addition to methods by which a receptor or molecule of interest is immobilized and used to bind an analyte, general methods exist for immobilizing members of a class of reactants. For example, protein A or protein G may be immobilized and used subsequently to bind specific immunoglobulins, which in turn will bind specific analytes. A more general approach is built around the strong and specific reaction between other ligands and receptors such as avidin and biotin. Avidin may be immobilized on a solid support or attached to a gel and used to bind antibodies or other reactants to which biotin has been linked covalently. That allows the production of surfaces to which a variety of reactants can be attached readily and quickly (see Savage et al., *Avidin-Biotin Chemist: A Handbook*. Pierce Chemical Company, 1992).

A wide variety of methods has been developed to detect reactions between immobilized molecules of interest and soluble reactants. The methods differ chiefly in the mechanism employed to produce a signal and in the number of different reagents that must be sandwiched together directly or indirectly to produce that signal. Examples include fluorescence (including delayed fluorescence) with the fluorescent tag covalently attached to the analyte, fluorescence involving soluble dyes, which bind to an analyte, and similar dyes wherein the fluorescence thereof greatly increases after binding an analyte. The latter can be used to detect nucleic acids. In more complex systems, including so-called sandwich assays, the result is the immobilization in the detection complex of an enzyme that, in combination with a soluble substrate, produces a preferably insoluble dye that may be fluorescent. Alternatively, the detection complex attached to the bound analyte may include a dendritic molecule, including branching DNA, to which is attached many fluorescent dye molecules.

In a related aspect, there are fluorescent dyes that bind directly to agents of interest. For example, rare earth metal chelates can be used such as, but not limited to, holmium, europium, terbium, samarium, ytterbium, neodymium and dysprosium. In a preferred embodiment, the rare earth metal is europium. In a further related aspect, heavy metals such as, but not limited to ruthenium can be used. Such dyes are available commercially from, for example, Molecular Probes, Inc. (i.e., SYPRO® Ruby Protein gel stain and SYPRO® Rose Protein blot stain).

Methods for making dental floss having attached short transverse fibers to give a brush-like configuration may be modified to allow attachment of reactants. Patterns encoding identifying information on strands or fibers may be employed in the form of small linearly arranged dots. In the development of multifiber endoscopy arrays, methods for checking the array have been developed in which a light beam or raster image is introduced at one end of the fiber bundle in such a manner that the light sequentially illuminates each fiber. The pattern of emitted light exiting the other end then is determined. If identical, no fiber is out of place.

The art of detecting bubbles or voids in liquid filled tubing is known and may depend on differences in refraction, light absorption or fluorescence as measured along individual tubes.

The art of using centrifugal force to fill short lengths of tubing with viscous media is evident to those trained in the arts.

Other methods include the use of microforges and automatic nanoliter injectors. For example, a microforge can produce glass micropipet tips with sizes of 10–30 µm. In one aspect, the capillary glass is produced from N-51-A material and has a softening point of 780° C. Tips can be pulled using a microforge (e.g., TPI Microforge at http//www.techproint-.com/microforge.htm/) and broken with forceps. Such tips can then be backfilled with oil (or other non-compressible fluid) and attached to an automatic nanoliter injector (e.g., Drummond "Nanoject II," Drummond Scientific Company Broomall, Pa.). Using such a device, a fully extended plunger can reproducibly withdraw substantially about 5 μl of fluid. In a related, aspect, viscous samples may be withdrawn in small steps allowing the sample to equilibrate in the tip before continued filling. Fibers made from such tips are amenable to sectioning by microtome, after which, in the case of hollow fibers, for example, the capillary tube cladding can be removed.

Microtomes for sectioning tissue blocks which may contain samples ranging from soft tissues to bone, often in blocks of embedding material (e.g. wax), are commercially available, as are a variety of techniques and arrangements for attaching sections to glass or plastic slides, for treating the slide automatically to remove some or all of the embedding media, and for systematically exposing the slides to a series of reagents.

Microtomes and other sectioning or cutting instruments capable of cutting assembled bundles of tubes into thin sections, and of maintaining the orientation of the component tubes after sectioning are known. Blade cutting may reduce contamination of binding components between cells of the microarray.

The microarrays can be of any thickness as required by the anticipated use thereof. Another determining factor might be the rigidity of the fiber bundles. It is likely the sections will be less than 1 cm in thickness. It is likely the sections will be less than 50 mm in thickness. In one embodiment, the thickness of the sliced fiber (or block) is between about 100 μm and about 1000 μm. In a preferred aspect, the thickness of the sliced fiber is less than about 50 μm. In a more preferred embodiment, the thickness of the sliced fiber is less than about 20 μm, as will be exemplified in further detail hereinbelow, sections can be on the order of microns in thickness.

The sections (as microarray chips) may be attached directly to adhesive surfaces on flexible films or on solid surfaces, such as glass slides. It is also feasible to attach sections (the word "section" is used here in place of "chip") at intervals along a film strip, with others interleaved therebetween. Thus, a set of about a dozen or more sections that are different may be placed in repeating order along the film, and the film then cut to give one set. For sequencing studies, one DNA insert may be amplified, labeled, and the hybridization pattern thereof to a large set of sections examined.

In one embodiment, the reagent can be incorporated into a paste or a gel that remains firm or quickly hardens after being extruded onto a solid phase. This is a variation of the conventional spotting techniques. Materials include, but are not limited to drying oils, conventional paint materials, molten materials which dry or cool to the point of becoming very solid, photo-, UV- or heat polymerizing or crosslinked materials and corresponding deposition treatment. For example, in one embodiment, coating a slide with calcium chloride and adding a thickened suspension comprising alginate, which further solidifies as the calcium ions dissolve and diffuse through the paste or gel is envisaged. In a related aspect, the binding partner and matrix as a core material are co-extruded as a coaxial outer coating.

By using a non-deformable bundle of fibers, one can cut or saw the bundle transversely thereby forming a large number of identical plates that are perfectly realignable. That permits highly consistent and reproducible arrays. By using an easily detectable different material for one or more fibers, as a means for registering the microarray alignment, realignment can be facilitated.

Most immunochemical or competition assays depend on a signal produced by a reagent other than the analyte. However, methods for fluorescently labeling antigens, such as proteins containing aliphatic amino groups in a complex mixture have been developed which are reproducible and quantitative. For example, CyDyes supplied by Amersham Life Sciences, and particularly, Cy2, Cy3 and Cy5 are useful. When the components of such labeled mixtures are reacted with an array of immobilized antibodies, each specific antibody binds to one of the fluorescently labeled analytes, and the presence of each of the specifically bound labeled analyte can be detected by fluorescence. That method can be improved further by exposing the bound antibody array to a solution containing known subsaturating quantities of each analyte protein in a non-fluorescent form, washing the array, and exposing the array to a test mixture of labeled proteins, thus producing a multiple competition assay.

Any of the conventional binding assay formats involving an immobilized binding partner may be used with the microarray systems of the instant invention. Briefly, the microarray may have either plural ligands or plural receptors and the analyte may be either plural ligands or plural receptors. Competing elements that bind to either the analytes or the microarray cells may be added. The sample may be labeled and/or the competing element may be labeled and/or the microarray cell may be labeled. The labels may be interacting with each other to make a detectable signal or product, or to quench a signal or product. The number of different combinations is in the dozens and any may be used in the instant invention as well as different combinations for different cells of the microarray assay.

Often several different clinical tests are required to define a particular disease. The multiple tests often are done serially, with one test or member of a battery of tests suggesting another, which in turn suggests a third test or group of tests, some of which are rarely done in local laboratories. There is therefore a need for inexpensive chips for the performance of a series of branching batteries of tests conducted simultaneously, using methods that produce accurate numerical results in a machine readable form, which are stable over time, and which are read by devices that can be compact and inexpensive relative to currently clinical analytical systems.

The availability of inexpensive microarrays testing for many disease markers simultaneously may provide indications of the severity of the disease and/or its prognosis. The diagnosis and subcategorization of each diagnosis is further enhanced in the present invention by measuring combinations of markers. Additionally, it may unexpectedly be discovered that the patient sample actually has a second disease present or that the disease may involve an additional organ system. Also, the overall health of the patient may simultaneously be measured. When performing one test at a time, as in the prior art, one must first suspect an abnormality in order to request a test for it. With the present invention, it is equally easy to measure 1 marker as 500 markers, which would lead to a qualitative difference in how diseases are diagnosed.

Many biochemical analyses require that the analytical procedure have wide dynamic range. Thus, enzyme and immunochemical assays often are done by determining the course of a reaction over a period of time, or by doing multiples analyses on a series of dilutions. Such analyses may be done by "reading" the microarrays at intervals during exposure to an analyte mixture of a developing reagent. In addition, parallel analyses using standards and blanks (controls) are required and are included. Large numbers of standardized inexpensive biochips will be required to meet such needs. The biochips may incorporate reactants of different classes that can, for example, detect and measure antigens, drugs, nucleic acids or other analytes.

In one embodiment, a microarray comprises a solid phase having a plurality of structures bound to its surface. In a related aspect, the structures comprise an immobilized agent of interest that is available for binding to a target and such a microarray can contain a plurality of different agents of interest in a corresponding plurality of different structures. In a preferred embodiment, the structures are permeable to the target and the structures comprise a material that includes, but is not limited to, plastics, gels, glass, sols, colloid suspensions and dextrans. Further, the structures may have hollow inner surfaces. In another embodiment, the structures are impermeable to the target and the target binds to the exterior boundaries of the structure.

These structures have three-dimensional form and are more than a single layer of molecules bound on the microarray solid support. These are either formed or carved out from a larger structure.

The structures in this embodiment may comprise the solidified contents of a tubular fiber where the outer tube has been degraded or removed leaving behind a microarray having structures resembling small pillars with a gap between them where the tubular material once was. The degradation or removal of the outer tubing may be accomplished by dissolving with a solvent, melting or subliming with heat or chemically degrading. Physical removal of the outer tubing where the solidified contents remain adhered to the solid support may be done by having the solidified contents (but not the tubing) bound to the solid support by physical cleavage with a knife or similar instrument, or by laser, electrical arc or other electromagnetic irradiation to destroy and thereby remove whatever material present between the pillars which remain.

The solid support may be precoated with a material, which will adhere the solidified contents but not the tubing, thus permitting easier removal. Also, the material may selectively adhere particles and tiny structures in the sliced fiber section without adhering the solidifying matrix.

Other techniques for producing a three dimensional structure include depositing a three dimensional structure directly on the solid support surface. This may involve a preformed structure or a fluid or semi-fluid material which solidifies very quickly before it spreads significantly or forms a few molecule thick layer. The preformed structure may be a long fiber that is cleaved once it adheres to the solid surface thereby depositing the structure. An analogy to the later method is seen in the food art. Chocolate chip cookie dough is semi-solid at the time it is extruded or deposited on the cookie sheet with the dough representing the matrix and the chocolate chips representing the agent of interest. Alternatively, a larger piece of material may be cut and pieces deposited such as the process shown in FIG. 8 without having the individual cubes (or other shapes) adhered to each other.

By coextruding two different materials, one may form a coaxial structure where the outer layer may be impermeable plastic to form a microwell or separate the inner layer having the agent of interest from other coaxial structures having a different agent of interest. Cleaving the top of an extruded or deposited structure to yield a smooth surface for contacting the target is frequently desirable for a number of different three dimensional structures made by a number of different techniques.

Arrays have numerous uses other than determining bioactive properties. Chemical interactions and reactions may be tested as well. Such an assay can, for example, enable testing different reactive chemicals simultaneously against a test substance or material to determine corrosion, electrochemical reaction or other interaction. That is particularly advantageous in the chemical formulations of plural substances such as in cosmetics, paints, lubricants etc. Alternatively, one may assay for desirable interactions between the analyte and all of the molecules of interest in the array.

The microarray of the present invention has many other non-microarray uses such as using the resulting surface for affinity chromatography, affinity separations, protein-protein binding to form protein complexes and the measurement for all of these.

The present invention also may also coat the surface with materials other than organic chemicals and biological materials. Different metals, anticorrosive coatings, decorative or instructional coatings, coatings for surface plasmon resonance (see U.S. Pat. No. 5,955,729), coatings for SELDI (see U.S. Pat. No. 6,020,208), combinatorial libraries of chemicals, and even coatings for depositing photoresists, electrically conductive coatings etc. such as are used in electronic integrated circuits.

A general problem with use of gels for the immobilization of reactants has been that reactants, which may attach to gel-immobilized agents of interest, require considerable time to difluse into and out of the gel. Where the detection is by fluorescence, inclusion of a dye absorbing the excited light into the gel limits detection to a region close to the surface. Inclusion of the ultraviolet light absorbing monomer, 4-methacryloxy-2-hydroxybenzophenone (Polysciences, Inc.) in an acrylic embedding medium can solve the problem. Addition of a quenching molecule such as DABSYL or DABCYL to accept the vibrating excited moieties before fluorescence emission also may be of use.

When one wishes to enhance binding between analyte and binding partners on the surface area of particles in a fiber of the microarray, one may etch the embedding matrix of each fiber, thereby exposing more of the surface area of particles in each fiber of the microarray.

When performing a binding assay, one may wish to encourage diffusion of the analyte into the microarray cell to increase ligand/receptor binding (sensitivity), to make the microarray more quantitatively reproducible and to enhance spectorphotometric detection if done by passing light through the microarray. To enhance diffusion through the microarray, one may force the ligand through the microarray gel material. That may be done by mounting the microarray on a porous membrane and passing the ligand and or ligand solution through the microarray by hydrodynamic, electrophoretic or mechanical means. For example, fluid may be flowed through the microarray by pressure difference on each side of the membrane. Fluid also may be drawn through by simply applying a stack of paper towels on the backside of the membrane to draw fluid through the microarray. As for electrophoretic means, a potential is applied across the microarray either across the entire microarray or using single point electrodes located on both sides of a single or group of cells of the microarray. Mechanical means may involve a pump of various configurations to mechanically push or pull fluid through the microarray by providing a pressure differential.

Using a porous membrane also has certain advantages in washing the microarray to achieve lower backgrounds. If porous particles or threadlike components are embedded within the fiber, sectioning through the porous particle or threadlike component may make the resulting structure more porous and allow greater surface area contact to both reagents and washing. Etching of an embedding medium or capillary also increases porosity and exposure to the immobilized molecules of interest.

If a porous particle is sectioned, preferably twice, larger channels allowing passage that is more fluid may be present. Fibers with sectioned particles may be mounted over permeable membrane supports or over holes in a solid base support. The result allows fluid to pass through the cells of the microarray.

By using the instant invention, one avoids the difficulties of individually spotting each cell on a solid phase or forming a compound at each cell. The former method is limited by human intervention and apparatus, as well as the ability to measure quantitatively small amounts of liquid. The latter technique is limited by the types of compounds that can be synthesized on the solid phase. Both prior art techniques are expensive and require elaborate automated equipment or tedious labor as each array is produced individually. By contrast, the instant invention is technically simple and quick where the "batch" is in the thousands to millions of microarrays. The only individual effort required for each microarray is the step of cutting.

Microarrays prepared from sets of stored reagents or by the synthesis of different reactive sequences or compounds on the base chip present difficult problems in quality control. With large arrays, each reagent in final form cannot be separately assayed before being used, nor can the correctness of the in situ synthesized sequences be assured until after a set of arrays has been manufactured. If errors or substandard components are discovered in a batch of arrays, all must be discarded. Those problems limit the use of "biochips" in routine clinical studies.

It is known that immobilized proteins and nucleic acids are more stable, especially in a dry state than in solution.

The agent of interest in the instant invention may comprise a very broad range of chemicals, complexes, biological cells or fractions thereof. Nucleic acids, many proteins, proteins which have been modified or are coated with detergents such as sodium dodecyl sulfate are soluble in organic solvents and a wide range of organic compounds and thus can be incorporated into polymerizing mixtures such as those used to produce plastics. Hence, it is technically feasible to produce long fibers of acrylic or other plastics each containing a different agent of interest using currently available extrusion technology for practice in the instant invention.

Large numbers of different and potentially new active compounds may be screened simultaneously by immobilization in fibers, bundling, sectioning and. forming a microarray. Peak fractions from separations, such as plant extracts, may be collected simultaneously and used to form a microarray. The microarrays then may be used in a large number of assay systems simultaneously, dramatically reducing the time and effort to screen all of the compounds present for whatever activity one chooses.

Particularly preferred are large numbers of proteins or peptides generated by mass techniques. Different fractions from a separation technique from a natural source provide a resource of many different proteins and peptides. A number of fractionation procedures are known to separate mixtures of many compounds. Different fractions or specific compositions may be used to form a single fiber. Two dimensional electrophoresis gels from serum and other tissue and natural sources produce thousands of different proteins separated on the gel. Each may be removed individually (e.g. cut, eluted etc.) from the gel and used as the molecule of interest to form a single fiber. In such a method, with different bundles being formed from different samples, protein differences between different samples may be readily compared.

When the immobilized macromolecules are antibodies, the microarray may be used to diagnose a variety of protein-based anomalies. A labeled second antibody to the protein of interest may be used to highlight the cell further. In addition, the array may be used to immobilize infectious agents, which have been either stained previously or which, are stained after immobilization. Thus, microbes from biological samples, e.g. serum or plasma, may be concentrated, stained with a fluorescent nucleic acid stain, such as TOTO-1 or YOPRO-1, and then allowed to find matching antibodies on the array. Then the bound analyte may be detected by scanning for fluorescence and identified by position.

It is equally a part of the instant invention to immobilize microorganisms or other molecules of interest and use the immobilized reagent to localize antibodies from a fluid from an individual, and then discover the location of the latter using a fluorescent anti-human antibody, thus diagnosing a disease which elicited antibody production in the first place.

Arrays have been prepared using phage display'with inserts from specific genes, using synthetic oligonucleotides, or, to a limited extent, using displayed antigens or antibodies. In the instant application, a population of peptide or antibody display phage may be used where each display phage is used to prepare a single fiber. In such an arrangement, the phage is large enough so that some portion of each surface molecule will remain embedded in the gel or plastic, while another part will be exposed. The molecule of interest may be bound to the fiber per se, entrapped inside the matrix or bound to a solid phase particle or tiny structure that is in or on the fiber. The phage, recombinant bacteria or other complex biostructure also may be fixed and the contained proteins cross-linked using glutaraldehyde or similar fixative, if desirable.

Each fiber may contain a mixture of molecules of interest. For example, during chemical synthesis, a number of isomers are prepared. It is convenient to not separate the isomers before forming a fiber in some circumstances. Likewise, when fractionating a mixture, forming a fiber with a mixture of receptors may be acceptable as total and complete isolation is difficult and time consuming.

When a collection of fibers are used, or in other embodiments wherein, for example, particles are embedded in a matrix to form a fiber, a filling material to maintain the relative positioning of the fibers along the length of the bundle may be desirable. Various glues and adhesives are known in the art. For example, a filling composition comprising an oil constituent with is a relatively high molecular weight aliphatic hydrocarbon of at least 600, an inorganic constituent and a block copolymer thicken yet reduce the viscosity of the material. An antioxidant also may be included. See, for example, U.S. Pat. No. 5,187,763.

The filling material selected is one that maintains the fibers in register, can be cut and does not interfere with any downstream procedures to which the microarray will be exposed. For example, other materials that can be used are polymerizable materials, such as a polyacrylamide.

The embedding matrix for the fibers may be black, opaque or otherwise adsorbent to emitted signals of a label to reduce cross talk between the cells in the chip. Additionally, any adhesive between the fibers may contain the same adsorbent material to reduce background between cells of the microarray. Optionally, a specific layer of the material may be placed between the fibers before the bundle is formed. When hollow fibers are used, the opaque material may be incorporated into the hollow fiber shell itself.

Arrays may have an entire set of antigens/antibodies etc. in the various cells along with controls to screen blood samples for common blood borne diseases before donated blood is provided for transftision. Likewise, certain symptoms have a number of common causes that may be screened simultaneously for using arrays. For example, urinary tract infections are common and may be caused by a large number of different bacteria of varying sensitivity to various antibiotics. The simultaneous testing for a number of different factors would save considerable time and expense.

In the course of using a chip of the instant invention, various known techniques and materials are used to reduce non-specific reaction. Thus, in the case of a protein-based assay, the non-specific sites on the chip contributed by the substance of the fiber or filament, the embedding material and essentially everything aside from the binding component of interest may be reacted with a blocking agent, such as albumin or milk, so that the blocking agent will bind to those areas not containing the binding component which could react with a ligand, analyte, reporter molecule or whatever would specifically bind to the binding component, as known in the art.

Arrays may have two or more identical cells made from different fibers but containing identical binding agents. That provides an internal quality assurance check for the array. Additionally, it is preferred for some of the cells to provide different concentrations of the binding component for quantitative measurement of an analyte. Those provide internal standards for the microarray for both qualitative detection and quantitative detection. For example, a series of cells may contain different concentrations of an antibiotic. When a sample microorganism is contacted with the cells and allowed to incubate, the absence of growth in one cell and the presence of growth in another cell provide an approximate minimal inhibitory concentration. The same can be done for determining minimal bacteriocidal concentrations when stained with a vital dye such as trypan blue or fluorescein acetate. Since a microarray may contain thousands of cells, one can determine the antibiotic sensitivity to numerous antibiotics simultaneously. Quantitative determination of other biological activities with either ligand or receptor immobilized in the gel may be used.

Essentially the same fiber may be used multiple times in the same microarray. That provides an internal quality control check and improves confidence in the binding assay. That also provides additional quantitative measurements if such an assay is performed to improve precision. Blank fibers, fibers with no molecule of interest bound thereto, provide a good negative control and should be used in every microarray.

Long filaments, capillaries or coaxial two-material filaments are arranged in parallel and then sintered or adhesively bonded to form bundles which are preferably resistant to deformation, and in which each strand or capillary is continuous from one to the other. The positional arrangement of fibers or capillaries should remain the same throughout the bundle. Filaments composed of two different types of material in coaxial formation may be used. The core material is made of a material, which can be dissolved, and the cladding being resistant to the same dissolving conditions. For example, strong alkali is capable of dissolving certain types of glass but not others. The dissolving step may occur before or more preferably after sectioning depending on the materials present.

Alternatively, the cladding may be dissolvable and the core resistant leaving isolated "islands" on a microarray attached to a backing sheet. In either situation, the space left by the dissolving step may remain empty or be filled with a diverse material. Partial dissolving to yield a porous material is also part of the instant invention. Porous materials have increased surface area, which is particularly desirable for binding assays.

Particles, especially porous beads, may also be "chemically sintered" to form a filament, sheet or inside of a capillary. That technique also may be used to adhere different fibers together. One such way is first to bind a molecule of interest to the particle. A blocking agent may be added to block any remaining active sites or adsorption areas on the particle. If not already done, the beads are packed in a tube or the hollow fiber. A chemically reactive compound which crosslinks or couples either the blocking agent and/or the molecule of interest and/or unreacted sites on the beads then is added and at the locations where the beads touch, chemical adhesion results. The tube or hollow fiber may remain in place or be removed. The molecules of interest in the internal pores of the beads are not touching and thus are not altered significantly. Alternatively, the pores of the beads may be filled with a hydrophilic solution and held by capillary action while the spaces between the beds are filled with a hydrophobic adhesive or setting liquid.

A representative example of chemical sintering is to adsorb Protein G on porous beads and then to add a gelatin blocking agent. The resulting beads are filled in a 1 mm plastic tube and then a protein crosslinking agent added, e.g. carbodiimide. After the reaction is complete, unreacted reagents are washed free and then any suitable antibody of interest is added thereto to bind to Protein G, thereby forming a fiber suitable for bundling and cleaving to make a microarray. Alternatively, the surfaces of the particles may be biotinylated first and avidin may be used as the crosslinking agent. One may use avidin labeled antibodies instead of adsorbing Protein G to the beads. Another alternative is to use relatively large porous beads and an adhesive or embedding medium to fill the spaces between the beads. When the fiber is sectioned, the beads are so large so as to be cleaved, thereby opening up the inside of the beads for the bound molecules of interest to be exposed. Hollow beads or microballoons may be used in lieu of porous beads, as molecules of interest encapsulated therein will be exposed on cleavage of the bead. The concept is the same as sectioning a tissue or embedded cell to expose and visualize intracellular features.

Additionally, one may use two different sets of beads: set one is porous and has the receptor/receptor binding substance bound thereto, and the second set is coated with highly reactive material or modified with a reactive group which will bind to the first set of beads or coating thereon. A tube first is filled with both beads in dry form, the tube shaken and then fluid is pumped therethrough permitting a reaction to occur thereby forming a solid fiber of beads. Alternatively, if the first set of beads is quite large, the beads may be added first (with or without fluid) and the second set added later so that the beads filter down through the spaces between the larger beads and react accordingly. The reaction between the beads may be through specific binding moieties or of a non-specific binding reaction to form a crosslinking of the beads into a sliceable solid. The second beads may be black to reduce stray light in the fluorescence detection. Such fibers may or may not allow for flow after sintering depending on desired utility.

In one embodiment, fibers containing beads can be used for solid phase synthesis. For example, a nucleotide/amino acid/sugar/chemical unit is first linked to a bead. The bead is preferably glass or a polymer, must be sinterable, yet allow the fiber to remain porous. A hollow fiber is filled with the beads and the beads are sintered together with heat, chemical, vapor, LW, solutions etc. In the situation of a polynucleotide binding partner in the fiber, one flows/pumps/uses negative pressure/uses capillary action to percolate reagents through the fiber where the reagent reacts with the nucleotide to produce a dinucleotide. After washing, the process is repeated until a sequence product of desired length is generated. The resulting fibers can be bundled before starting synthesis with a random or patterned addition of different nucleotides to prepare many different binding partners in the fibers. For example, ¼ of each bundle is infused with T and appropriate synthesis reagents, and ¼ each with G, A or C. The selection of which fibers to infuse with which nucleotides changes with each round of synthesis.

In a preferred embodiment, one can make all possible combinations, where the final product is usable in methods including, but not limited to, DNA sequencing, probe synthesis and primer synthesis. In another embodiment, by binding to various sequences of target DNA in a sample, a pattern of DNA/RNA sequences in the sample may be determined. Such a pattern may be a "fingerprint" for a particular abnormality, even in the absence of acquiring specific sequence information beforehand. The measurement of many different types of MRNA to generate a sample "transcriptome" by other techniques is known in the art.

In a preferred embodiment, such in situ solid phase synthesis is equally applicable for generating any other "heteropolymer" for fiber immobilization. In a related aspect, examples include, but are not limited to, polypeptides, polysaccharides, large numbers of organic chemical monomers which are "mix matched" to generate combinatorial libraries as well as polynucleotides. In a preferred embodiment, solid phase peptide synthesis is envisaged. Further, such solid phase synthesis methods for polynucleotides and peptides are well known in the art (e.g., U.S. Pat. Nos. 4,816,513 and 4,965,349) and are readily adaptable to bead-fiber immobilization as described in the present invention.

The solid phase particles inside a fiber may be chemically sintered together after synthesis of the oligomer/polymer/heteropolymer in situ. If the solid phase particles are labeled with a different specific binding partner such as biotin, then a solution of a corresponding specific binding partner, such as avidin or streptavidin may be pumped through the fiber and cause the particles to chemically adhere to each other.

After the fibers in the bundle are fused or otherwise adhered to each other in a fixed pattern, the bundle is cut transversely or at an angle into many thin disks and portions are optionally dissolved if desired. When hollow capillaries are used, the resulting disks may be used as channel plates for the amplification of optical images and light pipes. Regardless of whether rods or fibers are used, the thin disks also may be used as filters because of uniform hole size.

Each fiber segment in the sectioned two-dimensional array would contain relatively large numbers of binding components, such as DNA, RNA, or protein molecules. As a first step in the use of the final array, a solution, which can erode the plastic surface of the array very slowly, is washed over the surface. That is done at a rate, which will remove any biopolymer molecules that become loose. The wash then is continued, grading into a solution that will not erode the plastic. The array then may be dried and stored until used, or may be used at once. To assist in exposing reactive agents of interest in the plastic, particles on the surface are dissolved, forming a solution and exposing the molecules.

Because each fiber has the molecule of interest in the same form as will be present in the microarray, one can perform a quality control check on the fiber itself rather than using the entire microarray. That is particularly important when the microarray is used for diagnostic purposes. Sampling microarrays from a batch may be a quality control check but it does not actually check the microarrays being sold. By contrast, small slices of the fibers themselves are being used in the instant invention. Assaying the fiber itself represents an actual test of every microarray that has a slice of that fiber as a microarray cell.

By contrast, with solid phase in situ synthesis of a molecule of interest directly on each cell of the microarray, none of the actual compositions to be used containing molecules of interest is actually tested after synthesis. Rather, spot checking is relied on for quality assurance. In microarray manufacture by spotting liquid droplets on a solid phase, one may test the liquids as a quality control check. However, the liquid samples do not represent the quality of the dry molecules of interest immobilized on a slide. Therefore, the quality control check is not the same as the actual product being sold. Again, one lacks any quality assurance for the actual compositions in the cells of the microarrays being sold.

For quality control in the instant invention, the fibers may be individually assayed, assayed in ribbons or small groups, or assayed as part of the whole bundle before slicing. Furthermore, by testing one final microarray, one has effectively tested all of the microarrays as the composition of the fiber is the same as that portion of the final product.

The microarrays of the present invention have the ability to hold biological cells or pieces of tissue at the individual addressable locations of a microarray. This is particularly preferred with cells that can be suspended in a solidifying medium before being pumped into a hollow fiber. This finds particular application for leukemia or lymphoma cells that are naturally suspensable. Microarrays so produced are part of the present invention. Bacteria and other microorganisms may also be likewise used to prepare microarrays for screening candidate compounds for antibiotic properties or specific binding properties, such as from a serum source.

For clinical tests, regulatory approval of tests and systems and methods for making same is required. When chips are fabricated using photolithography and other technology derived from electronic chip making, the cost of individual chips is extraordinarily high, and the possibility of error when chips are made individually is very high. Since chips are made individually and used only once, quality control is difficult and there is no good way of proving that any given chip is satisfactory. The best that can be done is to test a large fraction of a batch at random. With the instant invention, a very large number of sections can be made from one composite assembly, and adjacent sections intercompared as well as those some distance apart. Statistical analyses will be able to predict the rate of errors that may occur. However, of even greater importance is the fact that since the sections can be made in large numbers and quite cheaply, it will be feasible to run duplicate analysis on clinical samples, and to run confirmatory analysis when important diagnostic results are obtained. The instant invention therefore makes feasible widespread and routine application of genetic analyses in the practice of medicine.

The key agent of interest components of the fibers is retained by the fiber by being immobilized therein. Immobilization may be accomplished by a number of techniques, known per se, such as entrapment in a matrix and chemical coupling, perhaps through a linking moiety through an amino, hydroxy, sulfhydryl or carboxyl moiety. Chemically attaching the chemical to a monomer or being used as a monomer to be polymerized also effectively incorporates the component. Binding also may be accomplished by a number of affinity techniques such as protein A or protein G for antibody attachment, ligand/receptor pairs such as biotin-avidin, HIV-CD4, sugar-lectin or through a ligand that has a receptor such as digoxigenin-antidigoxigenin. On the other hand, no specific attachment is required for situations where a gel or a non-gel, gelling matrix, such as wax, silicone polymers and silicone emulsions may be used. Liquid wax or a gelling agent simply is mixed with the key component and cooled to form a solid fiber by casting or extruding.

Arrays need not be assembled in a single step. Flat arrays consisting of a set of tubes arranged side-by-side may be prepared first, and the end of the array sectioned and tested. The flat arrays then can be attached together with a suitable adhesive to give a three-dimensional bundle. The use of intermediate flat arrays means that those can be prepared and stored, and custom two-dimensional arrays can be prepared by selecting and attaching together different one-dimensional arrays. The stepwise assembly procedure provides inspection at each step, minimizes losses due to errors or low binding efficiency of one rod or tubule, and provides flexibility to assemble new patterns of reactants.

Figure 5:
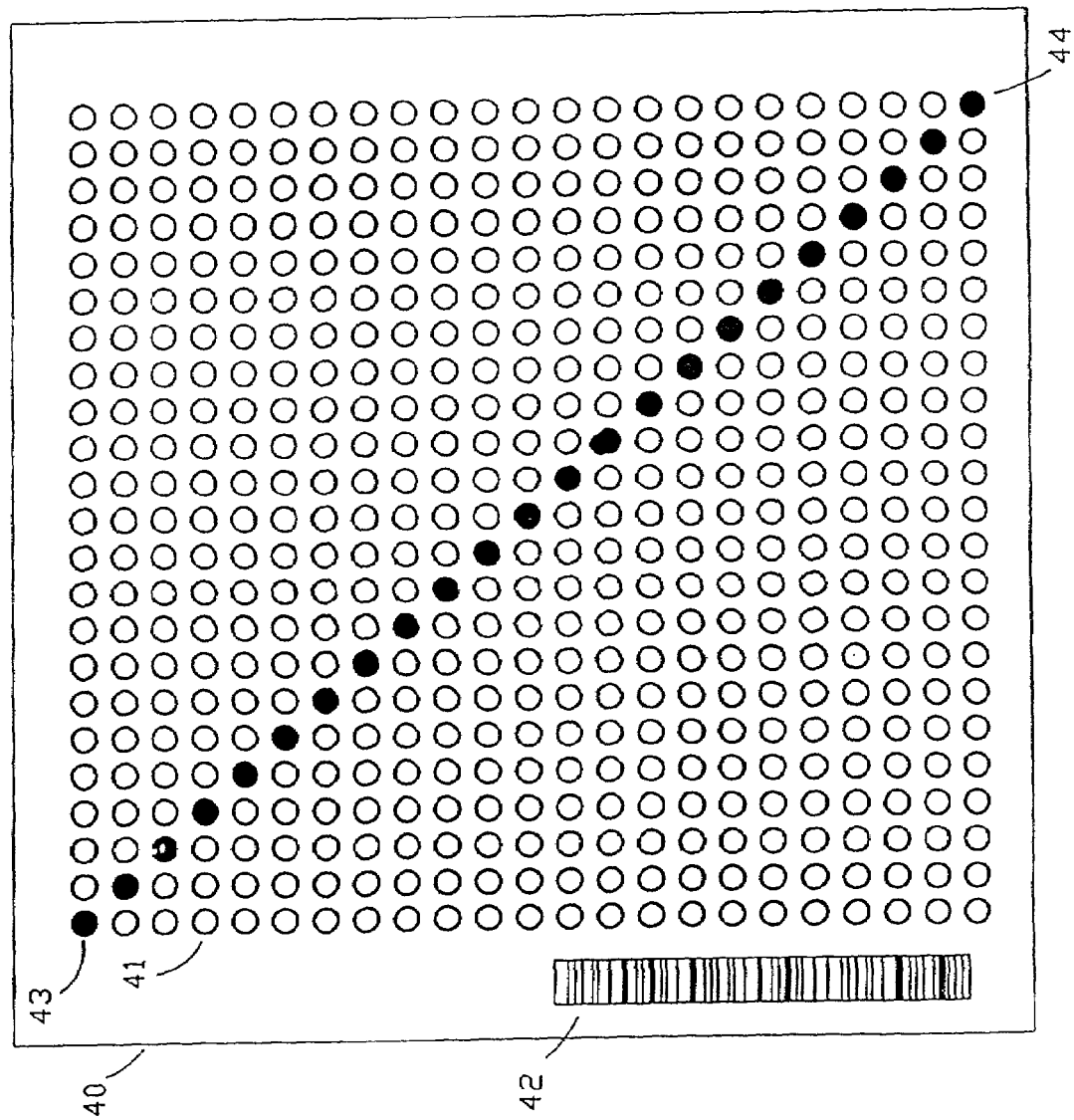
FIG. 5 is a schematic of a means for insuring that all fibers are maintained in their correct pattern before the bundle is sliced.

For general clinical use, it is important to have identifiers on the slide holding the chip, and identifiers may be integral with the chip itself. FIG. 5 illustrates chip 40 with array elements 41, and with a barcode 42 printed along one border to provide identification and orientation. In addition, small concentrations of dyes, usually non-fluorescent, may be incorporated into the polymers from made such that they present a pattern 43 to 44, for example, of one or more numbers, or one or more letters. It is also useful to have a few cells or elements which do incorporate fluorescent dyes and which serve to calibrate the fluorescence measurements. It is further feasible to introduce dyes into the contents of selected tubes to additionally identify them. Note that the diagonal line 43-44 further indicates that the horizontal rows of tubes from which the array is assembled, are in the proper order. If tubes in an array are out of alignment giving rise to the loss of one tube or rod in one line, this can be readily observed because the entire pattern will show a misalignment.

Figure 6:
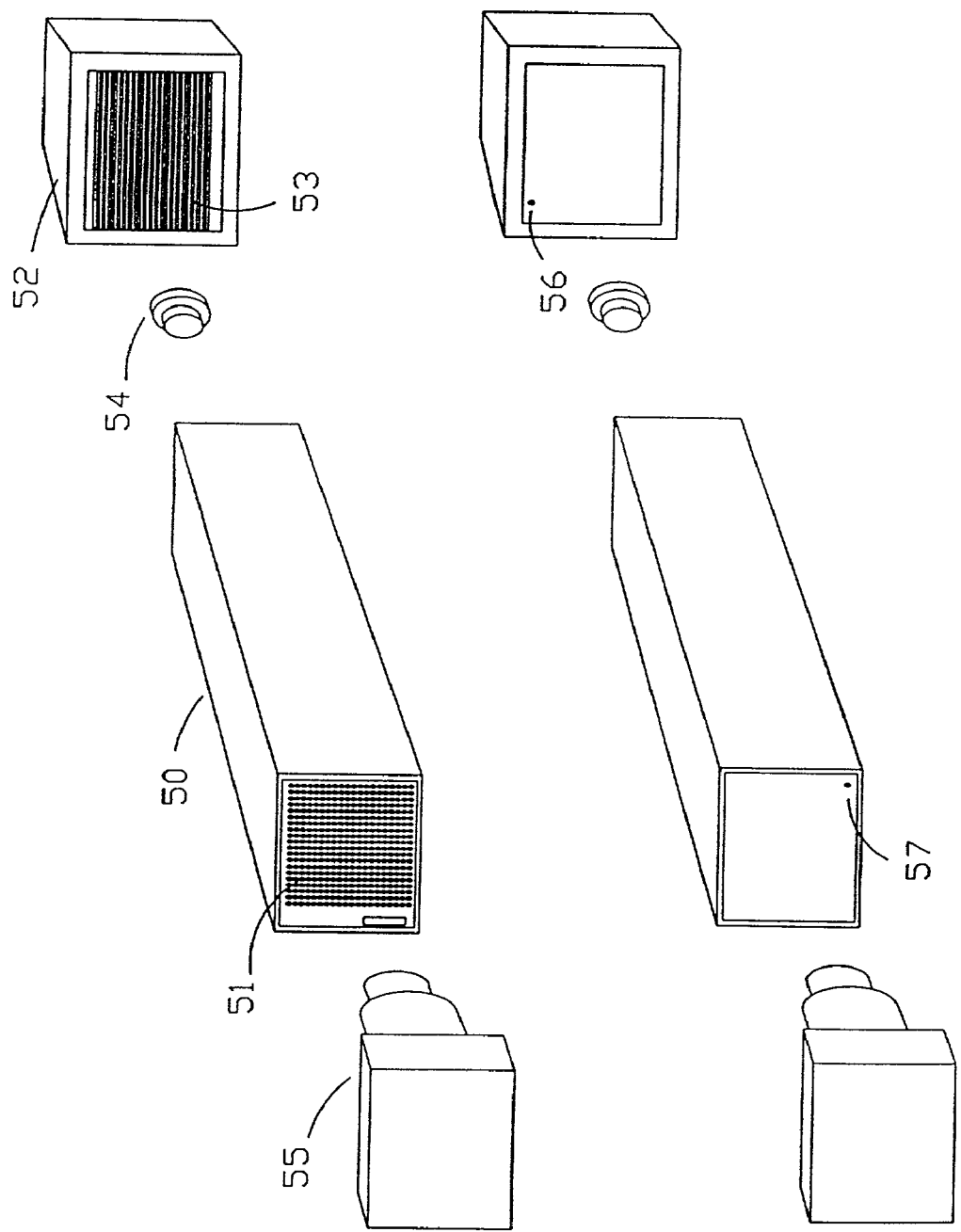
FIG. 6 is a schematic of means for identifying arrays.

The embedding material or adhesive used to hold the tubes in a bundled configuration may be opaque, while the tubes and preferably the contents thereof will conduct light along the entire length. As a final check on the orientation of array elements, one element at a time at one end of the bundle may be illuminated, and the light detected and related to array position at the other at the other end as shown in FIG. 6 where bundle 50 with fibers 51 is illuminated by a cathode ray tube (CRT) 52 generated raster 53 which is focused on the distal end of the bundle by lens 54, and the transmitted light recorded by CCD camera 55. Individual spots 56 yield signals 57 that are detected.

Figure 7:
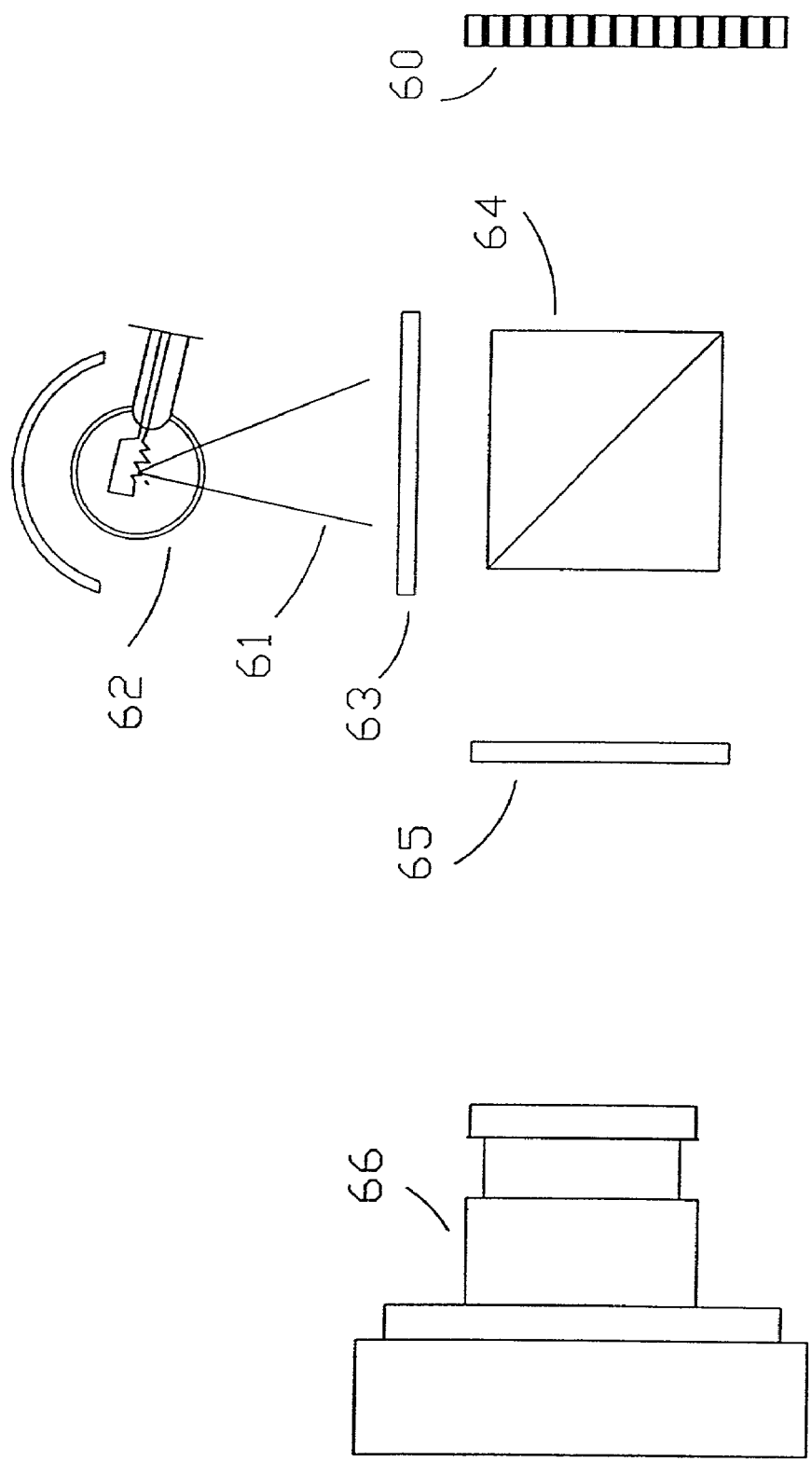
FIG. 7 is a schematic for scanning an array.

An arrangement for detection using epifluorescence is shown diagrammatically in FIG. 7 where chip 60 is illuminated by beam 61 generated by lamp 62, which passes through filter 63 to isolate light of a wavelength optimal for exciting fluorescence. A split-beam prism 64 directs the exciting light toward chip 60. The emitted light passes back through the split-beam prism after which the emitted wavelengths are isolated by filter 65 and detected by CCD camera 66. Different systems for detecting fluorescence patterns on chips are known to those skilled in the arts.

Figure 8:
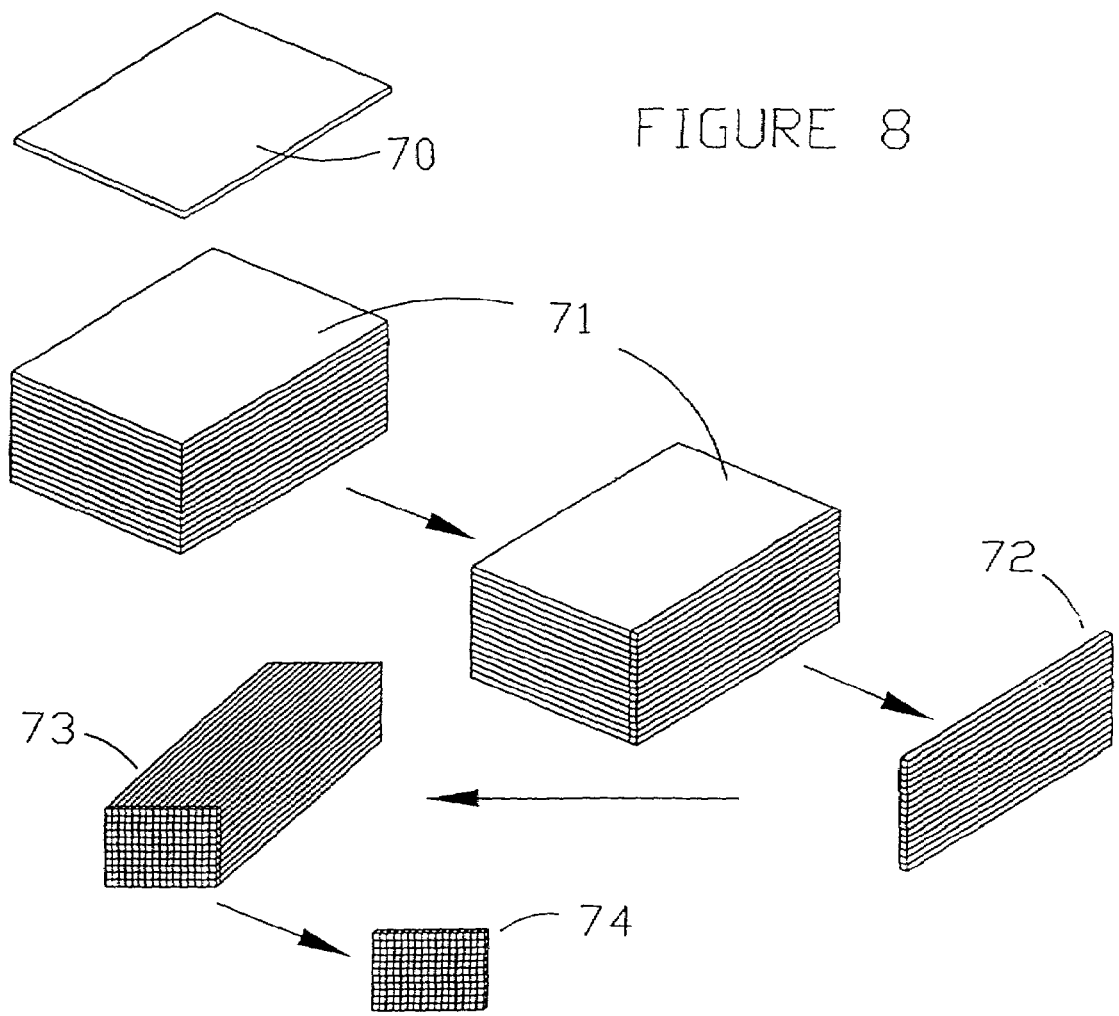
FIG. 8 displays an alternative way of forming a fiber bundle.

As an alternative method to forming fibers before bundling, one may first form the fibers by cleaving them from a larger material. In FIG. 8, a sheet of adsorbent material 70 is impregnated with a single ligand or receptor. That may be done by dissolving the compound in a solution and then impregnating a sheet of adsorbent paper (e.g. filter paper). A crosslinking agent may be added to attach the receptor to the cellulose base of the paper or other support. Alternatively, one can crosslink paper pulp to the receptor and then form the sheet of paper or felt. That alternative technique provides a more consistent and uniform distribution but requires greater amount of receptor. Either way, sheet (70) is produced. Many different sheets are prepared, wherein each sheet contains a different receptor.

The sheets then are stacked together (like a book) with adhesive and optionally an inert sheet (not impregnated, preferably black) as a spacer between each sheet of paper. That forms a book (71). One then takes the book to a paper cutter or similar sectioning instrument and a very thin strip (72) is cut which resembles the "ribbon" of FIG. 1, object (2). The rest of the process is similar to that shown in FIG. 1. Multiple strips (72) from different books are stacked to form a bundle (73) that then is cut transversely to form a microarray (74). An adhesive preferably is added to the ribbons to adhere them. Alternatively, an adhesive may be applied to a solid phase or the end of the bundle and the solid phase adhered to the bundle end before sectioning.

Other films, which adsorb protein, such as nylon films, may be used. Inert films such as polyolefin, activated using heterobifunctional photoactivatable crosslinking reagents or simple polyurethane film such as that of Thermedics may be used. One may use different proteins on different sides of the sheet or film and separate the sheets with an inert sheet to separate cells (sectors) and signals in the final microarray.

The fiber material is preferably glass, metal, plastic or other polymeric material. For coaxial composite fibers, the dissolvable component may be made of a much wider variety of materials. Each material may be a composite of two or more components. The fibers may act as light pipes or total internal reflection fiber optics to transmit positional alignment and information regarding chemical and biological reactions occurring on the surface. The fiber material preferably is chosen to support attachment of cells and molecules of interest such as oligonucleotides, peptides and polysaccharides. Hollow fibers may be used to store cells in fresh, frozen or dried condition. Light and electrons emitted directly or indirectly from a reaction or component inside the fiber, particularly a hollow fiber such as a capillary, may be amplified and easily detected when the fiber material is made of glass or other transparent or translucent material. The fiber material may contain a component to react with, detect or convert into another form, the light, electrons or other chemical components emitting from the components or reactions occurring in the fiber. Detection of chemiluminescent reactions in or on the fiber is a suitable method.

Gelling materials used in the present invention may be selected from a large number of such known materials. Polymers such as agarose, gelatin, collagen, xanthene, carrageenan, alginate, or a thermosetting, thermoplastic, chemosetting or UV polymerizing polymer may be used.

Non-polymeric gelling materials including waxes and clays may be used. Hydrogels are particularly preferred when a reaction occurring between the agent of interest and an added substance for interrogation requires an aqueous environment. The polymerizing agent or setting agent may be added after the fiber has been cast by submerging the cast in a solution of the agent or passing the agent along the outside of the fiber cast.

Hydrogels have many desirable features such as variable gel porosity, ability to bind proteins during or after polymerization, low non-specific binding, transparency, harmless polymerization byproducts, controllable polymerization open time, usable with a variety of solvents and so on. Isocyanate polyurethane liquid prepolymers are preferred.

Those may be modified further by using thickeners, gums, hardening and crosslinking agents, plasticizers and various combinations of gelling materials. In general, the gelling material should be sufficiently inert to not interfere with an interaction between the binding component and an analyte.

In the instant invention, an agent of interest is extracted into an organic solvent, which is miscible with either a thermosetting plastic mixture, or one that is polymerized chemically or by UV or ionizing radiation. That may be done by coating the agents with detergents or other reagents, which will enhance solubility under the conditions chosen. The mixture then is extruded into long fibers or cast into fibers. The fibers would be identified by tags on the end of the fiber or by tags on the rolls carrying the fibers, and/or by incorporating different dyes therein. A barcode also may be printed directly near the end of fibers. Thermoplastic polymers may be used when the embedded product is sufficiently thermostable. Some of the fibers may be colored differently to assist in the localization of specific ligands in the array or to identify the array itself.

The solvent may be miscible in the gelling material or may be extractable or volatile to render a porous final product. Porous products are particularly preferred with solid filament fibers that are self-supporting.

The fibers or the gelling material thereof also may contain a dye or other optical absorber so that only analyte/binding components on the surface of each cell are visualized. Such an improvement reduces the effects of diffusion rates through a gel or porous material that may change with temperature, time, type of carrier liquid, etc. A dye that adsorbs UV or emitted fluorescence will reduce fluorescence from non-surface analyte/binding component reactions.

Different dyes (fluorescent or non-fluorescent) may be incorporated into individual fibers. The permits the location of the individual fibers in the two-dimensional array to be confirmed.

The solid filaments or capillary tubes comprising the fibers may be adhered to each other by a variety of techniques. If the components are sufficiently heat stable, the fibers may be sintered together. Alternatively, a number of adhesives are known, including cyanoacrylate adhesives. The space between the fibers may be filled completely by adhesive or a monomer, which is polymerized. Thermoplastic and gelling materials also may constitute the adhesive by causing a large number of fibers to be held together in a block. Even inert materials such as Teflon® tubes may have the surfaces thereof made reactive with sodium metal in a hydrocarbon solvent to etch the surfaces. Non-chemical means, such as passing an electrical current through the fibers to fuse the fibers also may be used.

The open ends of the capillaries may be sealed against a flat plate, by pressing a deformable material against the surface, evaporating a plastic (e.g. paralene) on the surface, or by sealing with a chemical such as a thermoplastic or thermosetting plastic material.

There are two basic options for making two-dimensional arrays from such fibers. The first is to make and evaluate ribbons, and then to form a set of ribbons into a long rectangular bar, while the second is to make the bar at the outset, and then all of the fibers together in one step. The former option appears the more advantageous since the ribbons can be evaluated individually before being formed into a complete array. Once the two-dimensional array bar is formed, it can be sectioned using conventional microtomes to form a very large number of slices that can be attached, for example, to glass, metal, or plastic. Alternatively, one may first attach the solid phase material to the end of the bundle before sectioning the bundle. That may be performed by first coating either the end of the fiber bundle or the solid phase with, if necessary, an adhesive such as a cyanoacrylate adhesive or a pre-sectioning or post-sectioning sintering.

Dyed fibers would be visible in such arrays to confirm identification and orientation. In addition, the fibers can be dyed in such a manner that a visible pattern is formed if the array is made correctly, and the pattern may include a name or a number.

An advantage of the instant system is that very large numbers of arrays may be cut, and some fraction used for standardization. For example, if a bar 100 cm in length were constructed, and if the bar were cut at 100-micron intervals, then 10,000 arrays would be available. If the sections were 10 microns in thickness, then the number of arrays would be 100,000.

If the individual fibers were 100 microns in diameter, there would be 100 fibers per ribbon, and 10,000 in a bar of fibers with a cross-sectional area of 1 cm square. If there were 330 per ribbon, then the total number would be 108,900, approximately the number of expressed genes postulated to be present in the human genome.

The instant invention is the first array to have such a large number of different cells per unit area on a microarray without the binding agent being covalently attached to the chip. It is preferred for the instant invention to have at least 100, more preferably 250, 500, 1,000, 5,000, 10,000, 100,000 or a million or more cells per square centimeter of array. That is a much higher concentration than depositable cells formed by microfluidics in commercial microarrays.

To increase greatly the number of cells per square centimeter beyond even such high numbers, one may prepare a large fiber bundle with relatively large fibers and stretch or draw the bundle. While that makes the individual fibers thinner, the basic composition or orientation with respect to each other and cross-section geometry will not be altered. That technique has the twin advantages of allowing one to make more microarrays and smaller microarrays. By using conventional 5 micron porous particles (as in the Example below) and a plastic embedding medium such as a low melting point wax, the result is deformable or ductile fibers which may be drawn to very thin fibers of less than 20 microns in diameter. The field of drawing thermoplastic materials is well known per se. Even if not truly drawable through a die, one can pull or extrude plastic materials between rollers to lengthen and reduce the diameter of the fibers. With optional application of gentle heat, one need only pull the ends of the fiber bundle to generate the same lengthening and reducing of cross-sectional area. With smaller, porous particles, the fibers may be drawn to even thinner dimensions thereby permitting microarrays of up to at least about 10 billion cells per square centimeter of microarray.

In the field of fiber optics, bundles of optical fibers are heated and drawn into extremely thin optical fibers while retaining registry within the bundle. Likewise, candy canes and candy with cross-sectional designs are prepared by drawing a large block. Even glass beads used for hundreds of years also were prepared by such techniques.

High concentrations of cells (sectors) in a microarray have been achieved using photolithography where the molecule of interest is synthesized on the microarray cell. However, the compounds generated by photochemistry are limited. Further, chemically bound compounds interact differently from the same compounds when freely suspended. In a biological system, the active moieties may not be freely available for binding. By contrast, the binding agents of the instant invention may be merely entrapped in a matrix, fully retaining all chemical and biological activity.

When using porous particles and immobilizing the molecule of interest inside the porous particle, it may be desirable to retain a suitable fluid inside the pores and use an immiscible embedding medium. In that arrangement, the embedding medium may be incompatible with the molecule of interest or use in a binding assay, yet still be useable. For example, an aqueous solution may be used to protect proteins and a low melting point wax used to embed the porous particles.

The known photochemical processes of Fodor et al., Nature 364:555–6 (1993); Hacia et al., Molecular Psychiatry 3:483–92 (1998); and Fodor et al., Science 251:767–773 (1991) prepare short peptides and oligonucleotides covalently bound to the supporting chip. The process of amino acid or nucleotide synthesis inherently limits the practical length of the bound oligomer. Synthesis of entire proteins or genes on chips is not practical. Additionally, the secondary, tertiary and quaternary structure of the proteins may be important. By contrast, the instant invention permits such.

Many different arrays ultimately may be required, and some, especially those developed for the identification of infectious agents, may need to be changed at frequent intervals. Further, new disease-associated alleles will need to be incorporated into new arrays. To fill those requirements and allow changes and additions in arrays, it is important to have individual, stable fiber rolls available, and to have the rolls unambiguously identified. Each roll may be identified by the use of micro-stripes applied at short intervals along the roll. In addition, different tubes may have different colors, and non-fluorescent dyes incorporated into the gels to serve as identifiers, or bar coding, may be printed on individual fibers.

Not only can the chips of the instant invention be used to identify infectious agents by identifying characteristic nucleic acid sequences, for example, the chips also can be used for identifying intact bacteria, mycoplasmas, yeast, nanobacteria and viruses using arrays of immobilized specific antibodies.

The invention may be used for the identification of viruses or other infectious particles isolated by microbanding tubes. Such microbanding tubes are particular centrifuge tubes of stepped decreasing diameter from the open end to the closed end of the tube that enable concentration of desired low concentration biological elements in a small volume following appropriate methods of centrifugation. See, for example, WO99/46047. Thus, microbes from biological samples, e.g. serum or plasma, may be concentrated, stained with a fluorescent nucleic acid stain such as TOTO-1 or YOPRO-1, and then allowed to find matching antibodies on the array.

They then may be detected by scanning for fluorescence and identified by position. It is equally a part of the instant invention to immobilize microorganisms or other molecules of interest in the described chips, to use such chips to localize antibodies from body fluids, and then to discover the location of the latter using a fluorescent anti-human antibody, thus diagnosing the disease which elicited antibody production.

Because the bundle is maintained, additional fibers or ribbons may be added to the bundle as needed before sectioning additional arrays. That allows one to detect and measure newly discovered emerging diseases, new proteins, genes or compounds without recreating a completely new bundle.

The invention may be applied in an alternative fashion in which the bundles are stored at user sites, and the arrays sliced as needed. That arrangement may be useful for research purposes where identical arrays are required over the long term, but only a few are required at any one time.

Another alternative to slicing the bundle and using the sections thereof as separate microarrays is to perform the assay with the end of the bundle directly. After the assay is performed wherein a first sample could be applied to the cut cross-sectional surface, and washed off, a detector could image the result. One then may mount the bundle in a microtome device, if the assay were not already so mounted before the assay. A blade then could remove the used surface of the bundle, exposing a fresh surface for the next assay, which would repeat the same steps. The bundle thus could be used in one machine for a series of up to 100,000 or more assays performed one after another. That arrangement has certain advantages as optical or electrical detection may be performed through the bundle itself with fiber optic fibers or conductive fibers. The detection system may be attached continuously to the bundle while a more general light or electrical energy applied to the end being used for testing. Specifically note FIG. 6 where the testing technology may be adapted to a detection system.

The invention also allows different immobilization technologies, different classes of immobilized agents of interest, different classes of analytes and different types of detection methodologies to be employed on the same chip.

Since channels are reproducible between plates, the location of each channel or cell may be determined accurately by mechanical means. Reference markings on polished edges or other suitable locations further identify each cell in the array. Current commercially available computer driven two-dimensional drives of sufficient accuracy can be used so that each cell may be visualized or tested individually, or material may be added thereto or withdrawn therefrom.

Cut surfaces of each plate may be polished so that matching plates may be opposed to each other with little possibility of cross leakage. Surface treatment with a material repellant to the fluid to be eventually located inside each cell further reduces cross leakage. For example, fluorinating (Teflonizing) or silanizing agents repel water thereby generating sufficient surface tension to reduce cross leakage of cells filled with an aqueous solution.

After sections have been cut from a bundle, the sections generally are bound to a solid backing to provide structural support and ease of handling. The solid backing is typically a sheet of plastic or metal although other materials may be used. The attachment generally is done by a permanent adhesive or heat fision.

Individual cells in the array may be detected or visualized by scanning the entire array or portions thereof (e.g. one or a few cells) with a charged coupled device (CCD) or by illuminating one or a few channels at a time, such as by a condenser lens and objective lens. The absorbance and emission of light thus may be detected. An optical fiber bundle aligned and registering with the microarray may be used for optically detecting differences between the cells of the microarray.

Detection may be based on a large number of detectable labels including radioactive, enzyme, luminescent, electroluminescence, optically absorbent dye, magnetic, spin-labeled, oxidizers or reducers, chemiluminescence, or indirect labels which interact with a detectable component interacting with the agents of interest in the microarray. Detection may also be accomplished by measuring surface plasmon resonance, see U.S. Pat. No. 5,955,729. A suitable detectable labeling system is based on fluorescence, usually epifluorescence. That requires that the interrogating sample be labeled with one or more fluorescent dyes. The amount of test material required is very small since the dye would be applied to the arrays as a thin dilute film. Hybridization of nucleic acids would be done under conditions of carefully controlled stringency.

To distinguish selected channels, one either may seal off the selected channels and/or fill the channels with an easily detectable substance. Different colored inks, dyes and colored materials are particularly well suited as well as detectable components similar to or opposite from the detectable component(s) being detected in other cells. Printing methods with drying inks or plastics, sublimation, solvent containing an ink, or ink-jet printing may be used. The indicia so formed permits better alignment or easily detectable marking when the array is in use. That permits easy optical alignment.

Once the microarray has been used in a binding assay and the ligainds are bound to the receptors, in certain instances it may be useful to provide further identification of the ligand. In certain situations, one does not know the entire structure of the ligand from the receptor that specifically binds to it. For example, if the ligand is a cell, a macromolecular complex or a derivatized molecule with the derivatized portion acting as the ligand, etc., further analysis may be desirable. In that situation, one may elute the ligands from the microarray and collect the ligand for further analysis. For antibody/antigen binding, a pH 2–3 environment or other conditions should strip the ligands. For nucleic acid hybridization, raising the temperature should strip the ligands. A variety of other chemical, physical and electrical techniques for breaking such bonds are known per se.

To enhance specificity to the elution process, the substrate can be configured to enable maintaining a charge that would enhance trapping the biological agent of interest at a particular cell (sector). For example, if the agent of interest is a nucleic acid, each cell can be configured to carry a positive charge. A counterelectrode carries the opposite charge. Then, if necessary, a particular medium is placed into the cell and the charges in the electrodes reversed thereby releasing the ligands, in the example, nucleic acids, at that location. The counterelectrode also may be part of or contain appended thereto a micropipette to collect the elements released from the cell, see U.S. Pat. No. 5,434,049. Preferably, one uses a porous membrane and applies a current on opposite sides of the membrane.

The method used for analysis of the eluate may be capillary electrophoresis, mass spectrometry or a second binding assay. Convenient to mass spectrometry, the microarray itself may be introduced into a laser-matrix desorption system incorporated into a mass spectrometry system wherein bound molecules are desorbed and analyzed.

Once the analytes have been striped from the microarray, the microarray may be reused. That reuse process has the advantage of being standardized by multiple controls over time.

Additionally, if the receptor is attached to the matrix of the microarray by a cleavable linker, one can isolate the analyte by cleaving the linker. Different cells of the microarray may have different linkers or the same linker and subsequent purification may be needed before additional analysis.

The previous methodology for preparation of protein chips requires preparation, use and reuse of large numbers of proteins in solution. Proteins, nucleic acids, biological cells, other chemicals and complexes in solution are unstable and deteriorate over time. Even if frozen, repeated use may involve repeated freeze-thaw cycles that denature certain proteins as well. By contrast, immobilized proteins have been shown to be stable over long periods of time.

For the purposes of the instant invention, the term "substrate" refers to the glass capillary arrays with "major surfaces" referring to the open ends of the channel plate and "binding reagent" refers to the DNA, protein or antibody (collectively macromolecules), cells/microorganisms/cellular systems or other agent of interest.

The following examples are included for purposes of illustrating certain aspects of the invention and should not be construed as limiting.

EXAMPLE 1

Formation and Analysis of a Microarray

Antibodies were prepared by affinity purification by reversible binding to the respective immobilized antigens and subsequently immobilized on particulate supports (Poros G, made by PE Biosystems) in an Integral 100Q biochromatography workstation.

Each antibody support was made by trapping the antibody on a column of Poros G (commercially available Poros particles pre-coated with protein G, a bacterial protein capable of binding many immunoglobulins by the Fc domain) and subsequently cross-linking the antibody and the protein G with dimethylpimelimidate (following the PE Biosystems protocol) to immobilize the antibody covalently on the Poros particles. Such antibody columns can be reused (with an acid elution of bound antigen) more than 100 times in a subtractive mode, and therefore are extremely stable. Each antibody support was characterized to demonstrate specificity for a single antigen.

Antibodies directed against human serum albumin (HSA), transferrin (Tf), and haptoglobin (Hp) were used. A mixture of the three supports was made for use in serum subtraction. A total of three supports were used in tests with: 1) rabbit anti HSA, 2) rabbit anti-human Tf and rabbit anti-human Hp and 3) mixed anti-HSA, Tf and Hp. Unmodified BA Poros (commercially available streptavidin coated Poros), was used as a non-antibody control. Thus, a total of four supports were used.

Poros particles are roughly spherical and highly reticulated (with many internal crevices), having a diameter of approximately 5 microns. Attached proteins are distributed over the internal surfaces as well as the exterior surface of the particle. By embedding the particles in a suitable medium, a sliceable solid matrix in which the antibody was immobilized and fairly uniformly distributed was created. By exploiting the 3-dimensional nature of the support, a slice containing such particles offers greater capacity (for antibody and thus for antigen binding) than a simple flat surface as used in current microarrays.

Each of the four types of antibody-bearing particles was mixed with an approximately equal volume of 0.75% agarose melted in phosphate-buffered saline (PBS). The agarose for the rabbit anti-HSA beads contained green food coloring. Likewise, the anti-Tf and Hp agarose were colored blue, the mixed anti-HSA, Tf and Hp agarose was colored yellow and the Poros BA containing agarose was white (uncolored). Each melted agarose/bead combination was sucked into a length of one mm diameter plastic tubing of 10 cm in length attached to a 1 ml syringe and plunged in ice water. In several minutes, the agarose gelled into a jelly-like rod containing approximately 50% Poros beads by volume. The four rods thus obtained (each containing one of the four bead types above with a different protein coating) were laid into an aluminum channel with more melted agarose to form an array of 2×2 parallel rods embedded in a square cross-section bar of agarose.

After the bar gelled, the gel was removed from the aluminum channel mold, and transverse sections were prepared by slicing thin slices perpendicular to the axis of the bar (and the filaments) and mounted on a glass slide. The sections revealed a pattern of 4 circular areas (the filaments) containing embedded particulate material (carrying immobilized protein) surrounded by clear embedding matrix of agarose by microscopy. The circular zones of embedded beads were more stable and did not split.

To test specific protein binding to the beads in the four circular zones of a section forming the microarray, commercially available HSA and Tf protein were labeled with fluorescein isothiocyanate (FITC) on Cellite (from Sigma). Cellite is a commercial carrier for insoluble FITC. The proteins were dissolved in about 4 ml of 0.4M sodium bicarbonate buffer (~pH 8.3) and added to the dry FITC on Cellite in the following amounts:

| | |
|---|---|
| ~4.5 mg HSA | 30 mg FITC on Cellite |
| ~2.8 mg Tf | 18 mg FITC on Cellite |
| ~4.5 mg Serum Protein (20 µl) | 10 mg FITC on Cellite |

The reaction was conducted at room temperature for 30 minutes. The Cellite was removed by centrifugation, and the supernatant protein and unreacted dye placed in a centrifugal protein concentrator, where the protein was washed by repeated dilution and re-concentration in buffer. The fluid was centrifuged to remove the Cellite and supernatant recentrifuged with 4 ml sodium bicarbonate buffer until clear.

Sections of the 4-filament array were laid flat on a glass microscope slide and exposed to a solution of fluorescently labeled HSA. During the exposure of the section, the protein was expected to interact specifically with the antibodies present on two filaments (round areas on the section): the two filaments were those bearing antibodies to HSA and the mixed anti-HSA, Tf and Hp. Labeled HSA was not expected to interact with the filaments carrying antibodies to Tf alone or to the filament carrying streptavidin alone.

The sections were examined under an epifluorescence microscope equipped with a 500 nm low pass filter and a 510 nm high pass filter for fluorescein fluorescence detection and a 35 mm camera.

Prior to extensive washing, all four circular Poros zones showed bright fluorescence, with no discernable differences. The fact that the Poros zones showed higher fluorescence than the agarose matrix surrounding the filaments is an indication that the pores of the Poros particles remained unclogged and that the particle-containing zones thus allowed freer diffusion of labeled HSA into the sections.

The sections then were washed extensively in PBS and reexamined under the fluorescence microscope. The resulting images, captured on 35 mm color slides, demonstrate that after washing, the labeled albumin specifically bound to the two filaments containing HAS antibody and was removed from the other two, thus establishing the ability of the sections specifically to detect an individual protein. The two specifically labeled filaments were diagonally opposite one another in the 2×2 array, which was consistent with the diagonally opposite positions of the anti-HSA and mixed anti-HSA, Tf and Hp agarose filaments.

EXAMPLE 2

Manufacture and Use of Diagnostic Array Detecting Autoantibodies to Mitochondrial or Lysosomal Proteins Suspensions of whole isolated rat and mouse liver mitochondria, lysosomes and expressed proteins are suspended or dissolved in an aqueous buffer, at 10 mg/ml concentration, and optionally fixed with glutaraldehyde (1%). One ml of each preparation is mixed according to the kit instructions with 20 ml of JB-4 (Polysciences) catalyzed infiltration resin prepared by mixing 20 ml of monomer A containing 0.17 g of catalyst. After complete mixing, 40 ml of monomer B containing 0.17 g catalyst is added with stirring. When completely dissolved, 0.8 g of Accelerator is added, the mixture placed in a syringe and injected into 0.0625 inch internal diameter Teflon tubing under anaerobic conditions. Polymerization occurs at room temperature in approximately 50 minutes. The ends of the tubes then are heat sealed and stored cold until used, or are immediately extruded for use in preparing a fiber bundle. Bundles are prepared by laying 10 or more fibers in parallel, to make a single-layered array, in an elongated Teflon box. Additional JB-4 resin without protein then is poured in, the box briefly evacuated to remove air bubbles and the resin allowed to set. Several such flat arrays then may be stacked in parallel to make a three-dimensional grouping, and the whole grouping further vacuum impregnated to form a three-dimensional bundle. After polymerization, the bundle is cut with a steel or glass microtome knife to give sections 5–20 microns thick and the sections placed on glass slide. The sections are mounted using Plastic Mount®, or are dried and mounted with Poly-Mount® (Available from Polysciences).

Tests for autoantibodies are done by placing 0.25 ml of a 1:10 dilution of human serum on each chip and incubating the arrays at 25° C. for 20 minutes. The arrays then are rinsed in phosphate buffered saline four times, and then are immersed in a solution of goat anti-human globulin conjugated with horseradish peroxidase. After a further 20 minute incubation, the arrays again are washed four times with buffer, and then placed in a solution of 3,3',5,5'-tetramethylbenzidine in an organic base to which is added a hydrogen peroxide solution (0.02%) in a citric acid buffer. An insoluble blue color indicates the presence of autoantibodies.

EXAMPLE 3

Manufacture and Use of a Diagnostic Array Using Histological Embedding Support

Arrays are prepared which incorporate fixed infectious particles to be used to detect convalescent antibodies appearing late in the history of an infection. That is important in following sentinel populations to determine what infections are occurring.

Immuno-Bed GMA water-miscible embedding medium is made up as directed (Polysciences Inc.), and small batches are mixed with different suspensions of fixed selected viruses (average titer $10^9$/ml) or fixed bacterial cells (average $10^7$ particles/ml). The suspension is placed in a syringe and forced under pressure into Teflon® tubing of 1/16-inch internal diameter and allowed to polymerize at room temperature. The tubing is pre-treated with metallic sodium in an organic medium to provide a surface, which will adhere to epoxy resins. The polymerized fiber is stored in the coiled Teflon® tubing in the cold.

The arrays are assembled in bundles using jigs to hold the fibers in parallel array, after which the array is infiltrated with an epoxy resin. The finished bundle, which includes sections of Teflon® tubing, is sectioned and the sections mounted on glass slides using an epoxy resin mounting medium. The sections are washed for rehydration and then are exposed to convalescent antisera. The chips then are extensively washed and exposed to goat anti-human IgG with the covalently attached fluorescent dye fluorescein. Identification of convalescent antibodies is done by detecting and measuring fluorescence using a CCD camera.

EXAMPLE 4

Manufacture of Diagnostic Array Using Sintered Strips

Sintered polystyrene sheets 1/16 inch thick are cut into square cross-section strips and each exposed to dilute solutions of one monoclonal antibody to a series of infectious agents including viruses such as rhinoviruses, herpes simplex viruses, influenza virus type A, respiratory syncytial virus, varicella-zoster virus (chickenpox), mycobacterium tuberculosis, cytomegalovirus, Epstein-Barr virus, Hepatitis B Virus (surface antigen and separately core antigen) poliovirus (three strains) and others. The strips are rinsed, dried and glued together with an acrylonitrile adhesive to form a three-dimensional array that is sectioned to produce arrays 5–100 microns thick. Biological samples containing infectious viruses from individuals with viral diseases are fluorescently stained with the nucleic-acid specific dye YOYO-1 (Molecular Probes) and isolated and concentrated using centrifugal microbanding, see WO99/46047 supra, to concentrate the infectious particles into microliter volumes. The concentrated viruses are applied to the array and are agitated mechanically to move the virus particles over the array for one hour. The array then is washed, excess fluid removed by suction and illuminated with ultraviolet light at 490 nm. The image is captured with an Apogee CCD camera using a 520 nm filter. Quantitative data is obtained from the processed image using the PMIS image analysis program.

EXAMPLE 5

Manufacture and Use of Diagnostic Array Having Immobilized Oligonucleotides

Polystyrene beads (10–50 microns in diameter) from solid phase oligonucleotide synthesis with oligonucleotides covalently attached are suspended in buffer and packed into hollow glass fibers of 500 microns internal diameter under hydrostatic pressure initially and then under air pressure up to 500 psi to expel the supporting liquid. The fiber then is heated briefly under controlled conditions to partially sinter the contents. An array of fibers then is prepared following the methods in the examples above, embedded in a low viscosity epoxy resin with intermittent vacuum to remove air bubbles and then allowed to set. The bundle is sectioned using a diamond saw. The array is used in a flowthrough arrangement so that the materials thereon can be manipulated in a fashion similar to that conducted with larger multiwell microtiter plates as described in U.S. Pat. No. 5,843,767, supra

EXAMPLE 6

Manufacture of Multiwelled Plates

Commercially available glass capillary arrays (GCA) (Galileo) are in the shape of a thin disk having 2.5 cm×2.5 cm×0.5 mm thick dimensions. The GCA has approximately 50% of the area composed of 50µ holes or approximately 156,000 holes having a total volume of approximately 0.1 ml. The bottom surface of the GCA is glued to a Teflon® sheet with cyanoacrylate adhesive (SUPERGLUE).

EXAMPLE 7

Cloning and Replica Plating in Glass Capillary Arrays

A colony of Streptococcus pyrogenes Group A and a colony of Group B were picked from a plate and mixed together in nutrient agar forming a suspension of the bacterial cells (other microorganisms, animal or plant cells are equally applicable) and are diluted to an approximate concentration of 20,000 cells/ml of culture medium. About 0.1 ml of the suspension is applied to the surface of the GCA. That yields about 1 cell per 100 holes to ensure only single cell clones result. The GCA is placed in a sterile petri dish, covered and incubated overnight at 37° C.

Two additional sterile GCA's without a Teflon® sheet on the bottom are filled with 0.1 ml heated liquid culture fluid supplemented with 1% agarose, cooled until almost solidified and stacked directly on top of the GCA having cloned bacterial cells so that the holes from each GCA are in register. A top sheet of Teflon® is pressed on tightly and the stack is clamped together. The entire stack is turned upside down and incubated for five minutes at room temperature. The entire stack is turned sideways and incubated overnight at 37° C. The stack then is turned upright, unclasped and individual GCA's are separated. The original GCA is retained for fiiert use.

Each of the two added GCA's is placed in a glass flask, attached to a lyophilizer and vacuum dried for 1 hour. The GCA's are removed and 0.1 ml of FITC conjugated antibody to Streptococcus Group A (DIFCO) is added to each GCA and incubated at room temperature for 10 minutes. Each GCA then is blotted on an adsorbent tissue (KIMWIPE) to remove fluid. The microarray is washed by submersion in PBS and blotted dry again. The fluorescent holes in the GCA's and bacteria containing holes in the original GCA are detected using a CCD scanner which gives 12.5μ pixels and is capable of a resolution of 25μ needed to detect holes which contain cell clones.

The scanner is first set to scan for fluorescence and then for absorbance to detect the presence of bacterial clones. Absorbance is used to indicate presence of bacteria to align the holes of the two GCA's. Fluorescence is detected in some but not all of the holes containing bacterial clones in the original GCA and correspond to presence of Group S bacteria.

EXAMPLE 8

Selecting Monoclonal Antibodies

Monoclonal antibody-secreting hybridomas in suspension are diluted to approximately 20,000 cells/ml RPMI 1640+ 5% fetal bovine serum culture solution and 0.1 ml is added to the GCA of EXAMPLE 6 and the method of EXAMPLE 7 repeated except for incubation being at 37° C. in a $CO_2$ incubator for two days and the GCA's being pretreated with 10% fetal calf serum for 30 minutes. An additional GCA is filled with protein-free saline solution, stacked and clamped. The stack is not turned at all but incubated at room temperature for 15 minutes, unclasped and then vacuum dried as before. About 0.1 ml of FITC-conjugated goat anti-mouse immunoglobulin is added to the additional GCA, incubated, removed, washed and scanned for fluorescence as before. Antibody secreting hybridomas are deduced from the location of fluorescence on the GCA.

EXAMPLE 9

Screening Libraries of Proteins for Biological Properties

Human serum proteins are separated by 2-dimensional electrophoresis as per Baekkeskov et al., Diabetes 38(9): 1133–41 (1989). Two hundred spots are punched from the gel and the individual proteins dialyzed in 1 ml of PBS. One ml of the protein solutions is mixed with 40 mg of acrylamide monomer with catalyst and pumped into 1 mm internal diameter, one meter long polypropylene tubes, the ends heat sealed and each tube tagged. A number of control tubes are prepared with various dyes for easy identification of the correct orientation of the microarray when formed. The acrylamide is allowed to polymerize overnight. The tubes are aligned in a bracket and glued between rows as above. The bundle is cut by a microtome under freezing conditions into 10 micrometer thick slices and the microarray is immediately fixed on a plastic sheet.

Mouse monoclonal antibodies to the following antigens (Vector Labs) are individually contacted to a separate microarray, incubated, washed, dried and followed by contacting with FITC-conjugated (fluorescein-labeled) goat anti-mouse IgG and scanned as in EXAMPLE 8 above. Insulin, calcitonin, glucagon, epidermal growth factor, interferon, CEA, prostatic acid phosphatase and human IgG are among the common antigens tested. Both hormone levels and tumor antigen levels are determined in a semi-quantitative manner.

EXAMPLE 10

Rapid Antibiotic Sensitivity Testing

Microarrays are prepared in accordance with EXAMPLE 2 except for filling each tube with nutrient agar mixed with various antibiotics in the following configuration. Five two-fold dilutions across the effective spectrum of useful concentrations of the antibiotics, erythromycin, penicillin V, tetracycline, ampicillin, trimethoprim/sulfamethiozole, cefaclor, ofloxacin and nitrofurantonin and 10 two-fold dilutions of 34 new compounds, each a candidate for use as an antibiotic are used.

A colony of an unknown sample of *E. coli* grown from urine of a patient was suspended in 1 ml nutrient broth supplemented with either fluorescein acetate or trypan blue and placed on each of two microarrays and incubated at 37° C. The microarray is scanned for fluorescence and for absorbance at the beginning and after 30 minutes incubation. Microarray cells with detectable increases in fluorescence (scanned fluorescence minus fluorescence from initial scanning) were considered to have growing cells. Microarray cells with increases in trypan blue absorbance from the beginning to 30 minutes were considered to have dead cells. Minimal inhibitory concentrations (MIC's) and minimal bactericidal concentrations (MBC's) thus were determined. The possible effectiveness of the new candidate compounds likewise was deduced.

Another 1 ml of saline containing another suspended colony of the unknown sample of *E. coli* was plated on conventional Mueller-Hinton plates with antibiotic disks and incubated overnight. MIC's were determined the next day based on the diameter of the zone of inhibition. The MIC's from the microarray are comparable to standardized growth inhibition measurements. For example, for nitrofurantonin, the zone diameter from a 300 mcg disk in millimeters is >17 mm susceptible, 15–16 mm intermediate and <14 mm resistant which corresponds to a MIC in mcg/ml of <32, 64 and >128 respectively. Two-fold dilutions of nitroflrantonin in the microarray are at 16, 32, 64, 128 and 256 mcg/ml.

The method is repeated with known strains of *E. coli* having known differing levels of antibiotic resistance and with many different common microorganisms with different levels of antibiotic resistance. The results indicate which of the 34 candidate compounds are to be tested furer as potential antibiotics.

EXAMPLE 11

Anticancer Diagnostic and Drug Screening

Microarrays are prepared according to the method in EXAMPLE 2 with suspensions of various fresh cells from a leukemia patient, several leukemia cell lines (HTB, ATCC), normal peripheral white blood cells and normal bone marrow cells. The microarrays are treated by an alkaline-lysing and protease K-digesting reagent, heat denatured and a digoxigenin-labeled DNA probe for the following genes: N-myc, C-myc, K-ras, p53, HER-2/neu and a candidate DNA probe for diagnostic purposes, are applied thereto. Texas Red-labeled anti-digoxigenin antibody is added and the pattern and amount of binding are determined.

EXAMPLE 12

Hepatitis Testing

It is desirable to know the type of viral hepatitis and the stage of infection to best treat a patient. A microarray is prepared as in EXAMPLE 2 except that ten, 2-fold dilutions of mouse monoclonal antibodies to HAV, HBsAg, HBcAg, HCV, HDV and HEV and 2-fold dilutions of the same antigens are used. Three tubes of each are prepared and used in the microarray along with a pattern of controls. Approximately three drops of serum sample is contacted with the microarray, incubated in a 37° C. water bath for 10 minutes and washed four times with PBS. About 1 ml of a reagent of fluorescein-labeled monoclonal antibodies to non-overlapping epitopes of each of the antigens, fluorescein-labeled mouse anti-human IgG and rhodamine-labeled mouse anti-human IgM is added to the microarray, incubated for 10 minutes in a 37° C. water bath and washed four times with PBS. The microarray is scanned for fluorescence at both the wavelength of fluorescein and rhodamine emissions and the results determined for which cells of the microarray demonstrate fluorescence, the wavelength of light and the level thereof.

The microarray is designed for both initial diagnosis and for monitoring treatment and remission by detecting antigens and antibodies in convalescent serum. Two-fold dilutions and measuring the level of fluorescence at each cell provide quantitative results.

EXAMPLE 13

Screening Active Compound Candidates

Microarrays are prepared according to EXAMPLE 2 except 380 new candidate compounds are introduced into the fibers. Three drops of a solution containing the glutamate receptor 2 are added to the microarray followed by incubation at 37° C. for 10 minutes. The microarray is washed and dried as before. A 1:10 dilution of mouse monoclonal antibody to glutamate receptor 2 (Vector Labs) is added, incubated, washed and dried as before. FITC-conjugated goat anti-mouse IgG is added and the microarray scanned.

Fluorescent cells correspond to compounds that bind to the receptor. Since the receptor is involved in learning, memory, seizures and other neurological conditions, by binding the neurotransmitter glutamate, both agonists and antagonists are of pharmacological interest.

EXAMPLE 14

Formation and Analysis of a Microarray by Fluorescence

A microarray was prepared from cylindrical polymethacrylate fibers containing a) microbeads with immobilized antibodies to rat IgG, b) microbeads with immobilized antibodies to human IgG and c) no microbeads as a control. The array was formed by aligning the fibers in parallel along the long axis, sectioning with a microtome, then transferring the sections to glass slides. The slides there were tested in a fluorescent immunoassay to demonstrate specific protein binding to the beads as follows:

Two disposable columns, each containing about 0.5 ml of UltraLink Immobilized Streptavidin Plus beads (50–80 microns diameter, with a capacity of 10 mg of biotin-BSA per ml of beads, Pierce Chemical Co., Rockford, Ill.), were washed with phosphate buffered saline pH 7.2 containing 0.05% sodium azide. The slides were treated sequentially with five 1 ml solutions containing 0.5 mg of biotin labeled goat anti-human IgG on one column and 0.5 mg of biotin labeled goat anti-rat IgG on the other column. The columns there were treated with excess biotin, followed by washing with PBS.

The embedding material used was ImmunoBed (Polysciences, Inc., Warrington, Pa.) prepared according to the directions of the manufacturer. Dry catalyst (225 mg) was dissolved in 25 ml of ImmunoBed Solution A. To that solution was added 1 ml of hmmunoBed Solution B. The mixture was kept cold and then introduced into a four foot length of Teflon tubing (1/32 inch ID) using a syringe attached to the tubing. The tubing filled with ImmunoBed resin was allowed to stand undisturbed overnight at room temperature. The polymerized fiber could be removed from the Teflon tubing by trimming the end of the tubing with a single edge razor blade to expose the fiber, then gently pulling the fiber from the tubing.

UltraLink beads containing antibodies to human IgG and rat IgG were prepared as described above. About 0.5 ml of each were collected by centrifugation at 2000 rpm for 10 minutes then mixed with 5 ml of cold ImmunoBed solution (Solution A+catalyst+Solution B) prepared as described above. The beads then were centrifuged for 10 minutes at 2000 rpm at 5° C. That was repeated three times. The pelleted beads then were resuspended in 1 ml of the ImmunoBed solution and drawn into 1/32 inch ID Teflon tubing. The tubing was folded into a bundle, placed in a centrifuge bucket and then centrifuged for 10 minutes at 2500 rpm. The buckets were removed and left overnight at room temperature to allow the ImmunoBed to polymerize. The bundles were cut into sections by cutting the top end of the folds and the strands were extruded.

Two control fibers and two experimental fibers were cut to lengths of 1.5 cm each. The fibers were aligned along the long axis and placed in a groove in a Teflon block. A glass slide was placed over the fibers and clamped in place such that about 1 mm of each of the fibers was exposed. ImmunoBed solution (Solution A+catalyst+Solution B) was introduced to the exposed tips of the fibers and allowed to flow under the glass slide to fill the space around and between the fibers. The structures were left overnight at room temperature to allow complete polymerization. The array was removed from the mold and sectioned in a Leica Model RM-2155 Microtome. Thin sections (10 microns) were transferred to a glass slide containing a 20 µl droplet of water and the water was allowed to evaporate at room temperature. That left the sections firmly attached to the glass slide. Sections of 50 microns thick give more background fluorescence.

The 10-micron section prepared above and mounted on a glass slide was treated with 100 µl of normal rat serum (IgG containing), diluted 1:50 with PBS containing 1 mg/ml BSA, for 60 minutes at room temperature. The solution was drained from the slide, rinsed 1 time with 100 µl PBS/BSA, then washed three times with 100 µl PBS/BSA for 5 minutes before draining. After the last wash, 100 µl of R-Phycoerythrin-labeled affinity purified goat antibody to rat IgG (H+L) (Kirkegaard and Perry, Gaithersburg, Md.), diluted 1:100 with PBS/BSA were added and allowed to stand for 60 minutes at room temperature. The solution then was drained and washed 4 times as before. After fluorescent immunostaining, the section was viewed in an Olympus Model BX-40 fluorescent microscope (Olympus America, Inc., Melville, N.Y.) using a green filter (exciter filter 510–550 nm, barrier filter 590 nm). The four circular slices that comprised the 10-micron slice included 2 control slices, one slice containing beads with anti-human IgG and one slice containing beads with anti-rat IgG. The circular slice containing antibody to rat IgG was more highly fluorescent than the slice that contained anti-human IgG, and the 2 control slices, thus demonstrating the specificity of the reaction.

| Microarray Fiber | Table of Data Amount of Fluorescence | |
|---|---|---|
| Content | Observer #1* | Observer #2** |
| Antibody to Rat IgG | ++++ | 10 |
| Control (no antibody) | 0 | 0 |
| Antibody to Human IgG | ++ | 3 |
| Control (no antibody) | ++ | 2 |

*Fluorescence graded as 0, +, ++, +++ or ++++
**Fluorescence graded from 1–10

EXAMPLE 15

Detection Method for Microarray Using Rare Earth or Heavy Metal Conjugate Dyes

Antibodies are prepared by affinity purification by reversible binding to the respective immobilized antigens and subsequently immobilized on particulate supports (Poros G, made by PE Biosystems) in an Integral 100Q biochromatography workstation.

Each antibody support is made by trapping the antibody on a column of Poros G (commercially available Poros particles pre-coated with protein G, a bacterial protein capable of binding many immunoglobulins by the Fc domain) and subsequently cross-linking the antibody and the protein G with dimethylpimelimidate (following the PE Biosystems protocol) to immobilize the antibody covalently on the Poros particles. Such antibody columns can be reused (with an acid elution of bound antigen) more than 100 times in a subtractive mode, and therefore are extremely stable. Each antibody support is characterized to demonstrate specificity for a single antigen.

Antibodies directed against human serum albumin (HSA), transferrin (Tf) and haptoglobin (Hp) are used. A mixture of the three supports is made for use in serum subtraction. A total of three supports are used in tests with: 1) rabbit anti HSA, 2) rabbit anti-human Tf and rabbit anti-human Hp and 3) mixed anti-HSA Tf and Hp. Unmodified BA Poros (commercially available streptavidin coated Poros), is used as a non-antibody control. Thus, a total of four supports were used.

Poros particles are roughly spherical and highly reticulated (with many internal crevices), having a diameter of approximately 5 microns. Attached proteins are distributed over the internal surfaces as well as the exterior surface of the particle. By embedding the particles in a suitable medium, a sliceable solid matrix in which the antibody is immobilized and fairly uniformly distributed is created. By exploiting the 3-dimensional nature of the support, a slice containing such particles offers greater capacity (for antibody and thus for antigen binding) than a simple flat surface as used in current microarrays.

Each of the four types of antibody-bearing particles is mixed with an approximately equal volume of 0.75% agarose melted in phosphate-buffered saline (PBS). The agarose for the rabbit anti-HSA beads contained green food coloring. Likewise, the anti-Tf and Hp agarose are colored blue, the mixed anti-HSA, Tf and Hp agarose is colored yellow and the Poros BA containing agarose-is white (uncolored). Each melted agarose/bead combination is introduced into a length of one mm diameter plastic tubing of 10 cm in length attached to a 1 ml syringe and plunged in ice water. In several minutes, the agarose gels into- a jelly-like rod containing approximately 50% Poros beads by volume. The four rods thus obtained (each containing one of the four bead types above with a different protein coating) are laid into an aluminum channel with melted agarose to form an array of 2×2 parallel rods embedded in a square cross-section bar of agarose.

After the bar gels, the gel is removed from the aluminum channel mold and transverse sections are prepared by cutting thin slices perpendicular to the axis of the bar (and the filaments) and the slices are mounted on a glass slide. The sections revealed by microscopy a pattern of 4 circular areas (the filaments) containing embedded particulate material (carrying immobilized protein) surrounded by clear embedding matrix of agarose. The circular zones of embedded beads are stable.

To test specific protein binding to the beads in the four circular zones of a section forming the microarray, commercially available HSA and Tf protein are labeled with either europium chelate or ruthenium chelate using either SYPRO RUBY or SYPRO ROSE protein stain as directed by the manufacturer (Molecular Probes Inc., Eugene, Oreg.).

Sections of the 4-filament array are laid flat on a glass microscope slide and exposed to a solution of rare earth/heavy metal chelate labeled HSA. During the exposure of the section, the protein is expected to interact specifically with the antibodies present on two filaments (round areas on the section): the two filaments are those bearing antibodies to HSA and the mixture of anti-HSA, Tf and Hp. Labeled HSA is not expected to interact with the filaments carrying antibodies to Tf alone or to the filament carrying streptavidin alone.

The sections are examined under an epifluorescence microscope equipped with a 490 nm long pass filter or 600 nm bandpass filter for fluorescence visualization and a 35 mm camera or CCD camera. Excitation is carried out at 300 to 310 nm.

The sections then are washed extensively in PBS and reexamined under the fluorescence microscope. The resulting images are captured on 35 mm color slides or CCD camera (digitized at about 1024×1024 pixel with 12- or 16-grey bit scale levels assigned per pixel).

EXAMPLE 16

In Situ Solid Phase Synthesis of Polypeptides

Briefly, polystyrene beads (10–50 microns in diameter) from solid phase polypeptide synthesis with single amino acids covalently attached are suspended in buffer and packed into hollow glass fibers of 500 microns internal diameter under hydrostatic pressure initially and then under air pressure up to 500 psi to expel the supporting liquid. The fiber then is heated briefly under controlled conditions to partially sinter the contents. A solution for the amino acid subunits in a suitable solvent (e.g., N-methylpyrrolidine (NMP), dimethyl formamide (DMF), dichloromethane (methylene chloride) or chloroform) is mixed with the particles. The sub units are preferably N-protected amino acids, typically one of the 20 naturally occurring L-amino acids having protected α-amine groups, and protected carboxy, hydroxy, thiol and amine side chain groups. The subunit molecules infiltrate the matrices of particles until substantially all of the subunits are entrapped in (or associated with) the particles. N-α-protected amino acids are added to synthesize the peptide in 9-fluorenylmethoxycarbonyl (Fmoc) solvated in DMF. Activated forms of the amino acids can be added as symmetrical anhydrides, pentafluorophenyl esters and 1-oxo-2-hydroxy-dihydrobenzotriazine active esters. Alternatively, activating agents may be added to the polymer composition with the solvent. A useful activating agent for Fmoc-based synthesis is hydroxy-O-benzotriazole, tetramethyluronium hexafluorophosphate (HBTU), to which is added hydroxy-O-benzotriazole (HOBT) and diiospropylethylamine (DIEA). For Fmoc-based peptide synthesis, dimethylformamide (DMF)/N-methyl-pyrrolidone (NMP)/dimethylsulfoxide (DMSO) can be used.

The Fmoc protection group is first removed with piperidine and DNF, with the piperidine being thoroughly removed before addition of the next residue. A solution of HBTU, HOBT, DMSO, NMP and DIEA is mixed with the Fmoc amino acid to activate the amino acid to form a derivative which will react with the α-amino group of the growing peptide chain immobilized on the fiber. The fiber is then washed with DMF and the mixture containing the activated amino acid is flowed through the fiber to couple the amino acid subunit to the growing peptide chain. After coupling, the Fmoc protection group is removed and the above procedure is repeated for subsequent amino acids until the planned peptide is complete.

An array of fibers then is prepared following the methods in the examples above, embedded in a low viscosity epoxy resin with intermittent vacuum to remove air bubbles and then allowed to set. The bundle is sectioned using a diamond saw. The array is used in a flowthrough arrangement so that the materials thereon can be manipulated in a fashion similar to that conducted with larger multiwell microtiter plates as described in U.S. Pat. No. 5,843,767, supra.

EXAMPLE 17

Preparation of Omniclonal Antibodies Immobilized on Controlled Pore Glass

Omniclonal antibody to human serum albumin and Omniclonal antibody to alpha-2-macroglobulin (BioSite Diagnostics, San Diego, Calif.) were immobilized on controlled pore glass (505 A, 200–400 mesh, CPG, Inc., Fairfield, N.J.) by adsorption from a solution containing a polyurethane polymer (Hypol® G-50 Prepolymer, The Dow Chemical Company, Midland, Mich.). CPG (200 mg) was placed in a glass screw cap vial and 3.0 ml of a solution containing 20.5 mg Omniclonal antibody in 20 mM borate buffer, pH 8, and 0.4 ml of G-50 (10% in dry 2-propanol) was added. The samples were mixed gently for 3 hours at room temperature. The CPG particles were then washed by sedimentation 4 times with 5 ml of borate buffer then dried at 4° C. The amount of protein bound to the particles (30+/−5 mg/gm CPG) was determined by absorbance at 280 nm. The coated particles were tested for antibody activity by incubation with fluorescein-antigen for 1 hour, washed, and then viewed in a fluorescent microscope. Only those coated particles treated with cognate fluorescent antigens bound fluorescent antigens.

EXAMPLE 18

Preparation of an Antibody Array

In this example, Omniclonal antibody to human serum albumin (Omni-HSA) and Omniclonal antibody to alpha-2-macroglobulin (Omni-α2M) were immobilized onto controlled pore glass. The particles were suspended in a solution of 7.5% acrylamide with ammonium persulfate and aspirated into polymethyl methacrylate(PMMA) capillary tubing (1000μ OD×750μ ID, Paradigm Optics, Inc., Pullman Wash.) and allowed to gel. Short lengths (1.5 cm) of each were then transferred to BEEM capsules (Polysciences, Inc. Warrington, Pa.) and a solution containing 80% methyl methacrylate (MMA), 20% butyl methacrylate (BMA) and 0.5% benzoin methyl ether was added to fill the tubes. The tubes were capped and exposed to UV irradiation at 1 cm for 2.5 hours at room temperature, then allowed to cure overnight at room temperature. Thin sections (25μ) were prepared, mounted on glass slides and treated with fluorescein-human serum albumin (0.1 mg/ml in PBS containing 1 mg/ml BSA). The sections were then washed with PBS containing 0.5% Tween 20 and viewed in a fluorescent microscope. Only samples containing CPG with Omni-HSA exhibited significant fluorescence.

EXAMPLE 19

Immobilization of Antibody in a Methacrylate Polymer with Retention of Antibody Activity A cold mixture comprised of 1 part aqueous Omniclonal antibody (Omni-HSA and Omni-$\alpha_2$M) and 10 parts methyl methacrylate (MMA)/polyethylene glycol methacrylate (PEGMA)/polyethylene glycol dimethacrylate (PEGDMA) (1:1:1) was vortexed vigorously then polymerized by UV irradiation at 1 cm for 1 hour then cured overnight at 4° C. The resulting blocks were not clear in appearance, but rather had many small globules suspended throughout the block. Thin sections (25μ) were prepared, mounted on glass slides and treated with fluorescent antigen. The globules apparently resulted from a phase separation in which the aqueous, antibody-containing phase became suspended in the acrylate polymer. Furthermore, the antibodies in the globules retained their activity, as demonstrated by their ability to specifically bind fluorescent antigen.

EXAMPLE 20

Immobilization of Antibody in a Methacrylate Polymer By Sonication and Retention of Antibody Activity In an attempt to disperse the globules in a more homogeneous fashion, a 10% suspension of Omniclonal antibodies in MMA/PEGMA/PEGDMA (1:1:1) was sonicated for two minutes. The suspension was then aspirated into PMMA capillary tubing (1000μ OD×750μ ID) and polymerized by UV irradiation. The tubing was then embedded in MMA/BMA by UV irradiation at 1 cm for 1 hour at room temperature. The resulting blocks were sectioned and the sections treated with fluorescein-HSA. For this experiment, both Omniclonal anti-HSA and Omniclonal $\alpha_2$M were used.

EXAMPLE 21

Preparation of an Antibody Array

An antibody array was prepared as in Example 2 except the CPG particles with immobilized Omniclonal antibodies were packed in PMMA capillary tubings with MMAN-PEGMA/PEGDMA as binder, then the tubings were arranged in hexagonal patterns and embedded in MMA/BMA to form small cylinders. Two unit devices were prepared in which experimental (filled circles) and control (open circles) samples were arranged as shown in the following schematic diagram.

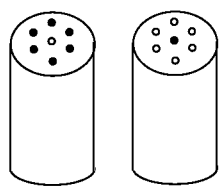

Thin sections (25µ) of both of these units were prepared and treated with fluorescein-HSA.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

All patents and references cited herein are explicitly incorporated by reference in their entirety.

REFERENCES

Books

Hermanson, Greg T. Bioconjugate Techniques. Academic Press, New York. 1995, 785 pp.

Hermanson, G. T., Mallia, A. K. & Smith, P. K. Immobilized Affinity Ligand Techniques. Academic Press, 1992, 454 pp Periodicals Ogura, M., Agata, Y., Watanabe, K., McCormick, R. M. Hamaguchi, Y., Aso, Y., and Mitsuhashi, M. RNA chips: Quality assessment of RNA by microchannel linear gel electrophoresis in injection-molded plastic chips. Clin. Chem. 44: 2249–55, 1998.

Johnston, M., Gene chips: Array of hope for understanding gene regulation. Cur. Biol. 8: R171–4, 1998.

Jordan, B. R., Large-scale expression measurement by hybridization methods: from high-density membranes to "DNA chips". J. Biochem. (Tokyo) 124: 251–8, 1998.

Pevzner, P. A., Lysov, Yu. P., Khrapko, K. R., Belyavsky, A. V., Florentiev, V. L. and Mirzabekov, A. D. J. Biol. Struct. Dyn. 9: 399–410, 1991.

Hacia, J. G., Brody, L. C., Collins, F. S. Applications of DNA chips for genomic analysis. Mol. Psychiatry 3: 483–92, 1998.

Ramsay, G., DNA chips: State of the art. Nat. Biotechnol. 16: 40–4. 1998

Kozal, M., Chee, M., Shah, N. Yang, R., Gingeras, T. Development of DNA chips for the rapid sequence analysis and the development of drug resistant mutations for the HIV protease and reverse transcriptase genes. Natl. Conf. Hum. Retroviruses Relat. Infect. ($2^{nd}$) 1995:93.

Fodor, S. P., Rava, R. P., Huang, X. C., Pease, A. C., Holmes, C. P., Adams, C. L. Multiplexed biochemical assays with biological chips. Nature 364: 555–6, 1993.

Fodor, S. P. A., Read, L. J., Pirrung, M. C., Stryer, L., Lu, A. M., and Solas, D. Light-directed spatially addressable parallel chemical synthesis. Science 251: 767–773, 1991.

Cheng, J., Shoffner, M. A., Hvichia, G. E., Kricka, L. J., and Wilding, P. Chip PCR II. Investigation of different PCR amplification systems in microfabricated silicon-glass chips. Nucleic Acids Research 24: 380–5, 1996.

Woolley, A. T., and Mathies, R. A. Ultra-high-speed DNA fragment separations using microfabricated capillary array electrophoresis chips. PNAS USA 91: 11348–52, 1994

Southern, E. M., DNA chips: Analyzing sequence by hybridization to oligonucleotides on a large scale. Trends in Genetics. 12: 110–5, 1996.

Birnbaum, S., Uden, C., Magnusson, G. M., and Nilsson, S. Latex-based thin layer immunoaffinity chromatography of quantitation of protein analytes. Analytical Biochemistry. 206: 168–171, 1992.

Bellara, S. R., Cui, Z., MacDonald, S. L., and Pepper, D. S. Virus removal from bioproducts using ultrafiltration membranes modified with latex particle pretreatment. Bioseparations 7: 79–88, 1998.

Van Oss, C. J., and Singer, J. M. The binding of immune globulins and other proteins by polystyrene latex particles. J. Reticuloendothelial Society 3: 29040, 1966.

Arlinghaus, H. F., Kwoka, M. N., and K. Bruce Jacoson Analysis of biosensor chips for identification of nucleic acids. Anal. Chem. 69: 3747–3753, 1997.

Wang, J., Cai, X., Rivas, G., Shiraishi, H., and Dontha, N. Nucleic-acid immobilization recognition and detection at chronopotentiometric DNA chips. Biosensors & Bioelectronics 12: 587–599, 1997.

Livache, T., Bazin, H., Caillat, P., and Roget, A. Electroconducting polymers for the construction of DNA or peptide arrays on silicon chips. Biosensors and Bioelectronics 13: 629–634, 1998.

Syvanen, A-C. From gels to chips: "Minisequencing" primer extension for analysis of point mutations and single nucleotide polymorphisms. Human Mutation 13: 1–10, 1999.

Shevalier, A., Mikhailov, M., and Nikolaeva, I. New fast low-cost method of HIV diagnostics based on carbon-conjugated antigens. Abstr. PB0420 Itent International Conferences on AIDS. Abstr. Book Volume 1. International Conference on STD. Yokohama Japan, 7–12, August, 1994.

Inomata, Y., Wada, T., Handa, H., Fujimoto, K., and Kawaguchi, Preparation of DNA-carrying affinity latex and purification of transcription factors with the latex. J. Biomaterial Sci., Polymer Edn. 5: 293–301, 1994.

Balhorn, R., Allen, M., Tensch, B., Marzrimaz, J. A., Balooch, M., Siekhaus, W., Imaging of DNA molecules deposited on graphite, in "DOE/NIH Human Genome Contractors. Grantee Workshop", Santa Fe, 34 (1989).

Sundarababu, G., Gao, H, and Sigrist, H. Photochemical linkage of antibodies to silicon chips. Photochemistry and Photobiology 61: 540–544, 1995.

Regnier, F. E., He, B., Lin, S., and Busse, J. Chromatography and electrophoresis on chips: Critical elements of future integrated, microfluidic analytical systems for life science. Trends in Biotechnology 17: 101–106. 1999

Patents

U.S. Pat. No. 5,843,767 Microfabricated, flow-through porous apparatus for discrete detection of binding reactions.

U.S. Pat. No. 4,289,623 Hollow fiber dialysis

U.S. Pat. No. 3,976,576 Dialyzer cartridge—Also, use of dialyzer cartridge by filling hollow fibers and embed protein in fibers as they are formed before the cartridges are cut.

What is claimed is:

1. A microarray comprising a solid phase support and at least about 500 cells per square centimeter wherein each cell contains an agent of interest that is not chemically bound to the solid phase support and a plurality of structures bound to said solid phase support, wherein each of a plurality of structures has an immobilized agent of interest available for binding to a target, wherein the target is a binding partner for the agent of interest, and wherein the microarray contains a plurality of different agents of interest in a corresponding plurality of different structures and, wherein the structures are permeable to the target.

2. A microarray of claim 1 comprising a solid phase support and at least about 500 cells per square centimeter wherein each cell contains an agent of interest which is a macromolecule, a microorganism, a plant or animal cell, an organelle or a fraction of a biological cell.

3. The microarray of claim 1 containing at least about 1,000 cells per square centimeter.

4. The microarray of claim 1 containing at least about 5,000 cells per square centimeter.

5. The microarray of claim 1, wherein the structures are a gel.

6. A microarray comprising a solid phase support and at least about 500 cells per square centimeter wherein each cell contains an agent of interest that is not chemically bound to the solid phase support and a plurality of structures bound to said solid phase support, wherein each of a plurality of structures has an immobilized agent of interest available for binding to a target, wherein the target is a binding partner for the agent of interest, and wherein the microarray contains a plurality of different agents of interest in a corresponding plurality of different structures, wherein each of the structure forms a hollow chamber with the agent of interest immobilized on an inner surface of the hollow chamber.

7. The microarray of claim 6 containing at least about 1,000 cells per square centimeter.

8. The microarray of claim 6 wherein the agent of interest is a macromolecule, a microorganism, a plant or animal cell, an organelle or a fraction of a biological cell.

9. A microarray comprising a solid phase support and at least about 500 cells per square centimeter wherein each cell contains an agent of interest that is not chemically bound to the solid phase support wherein the solid phase support has a flat surface, and a plurality of structures projecting away from the plane of the solid phase support, wherein each of the plurality of the structures has an agent of interest bound thereto, and wherein the microarray contains a plurality of different agents of interest in a corresponding plurality of different structures.

10. The microarray of claim 9 containing at least about 1,000 cells per square centimeter.

11. The microarray of claim 9 wherein the macromolecule is a protein.

12. The microarray of claim 9 wherein the agent of interest is synthesized prior to contacting the solid phase support.

13. The microarray of claim 9 wherein each cell is formed by a solid material adhered to said solid phase support and wherein each solid material contains an agent of interest.

14. The microarray of claim 9 wherein the structures are made of impermeable material and the agents of interest are immobilized on a surface thereof.

15. The microarray of claim 9 wherein the structures were formed by solid material between the structures being removed.

16. The microarray of claim 9 containing at least about 5,000 cells per square centimeter.

17. The microarray of claim 16 containing at least about 10,000 cells per square centimeter.

18. The microarray of claim 17 containing at least about 100,000 cells per square centimeter.

19. The microarray of claim 9 further comprising a hydrophobic material between the cells on the solid phase support.

* * * * *